US005789587A

United States Patent [19]

Fisher et al.

[11] Patent Number: 5,789,587
[45] Date of Patent: Aug. 4, 1998

[54] HETEROCYCLIC-FUSED LACTAMS PROMOTE RELEASE OF GROWTH HORMONE

[75] Inventors: Michael H. Fisher, Ringoes; Helmut Mrozik, Matawan; William R. Schoen; Thomas L. Shih, both of Edison; Matthew J. Wyvratt, Mountainside, all of N.J.

[73] Assignee: Merck & Co., Inc., Rahway, N.J.

[21] Appl. No.: 744,296

[22] Filed: Nov. 6, 1996

Related U.S. Application Data

[62] Division of Ser. No. 166,440, Dec. 14, 1993, Pat. No. 5,606,054.

[51] Int. Cl.$^6$ .......... A61K 31/55; C07D 487/04
[52] U.S. Cl. .......... 540/521; 540/455; 540/460; 540/461; 540/491; 540/503; 544/48; 544/105; 544/350; 548/453; 546/114; 514/215
[58] Field of Search .......... 540/455, 460, 540/461, 491, 503, 521; 544/48, 105, 350; 546/114; 548/453

[56] References Cited

U.S. PATENT DOCUMENTS

| 3,239,345 | 3/1966 | Hodge et al. | 514/213 |
| 4,036,979 | 7/1977 | Asato | 514/213 |
| 4,411,890 | 10/1983 | Momany | 514/213 |

FOREIGN PATENT DOCUMENTS

| 253310 | 7/1987 | European Pat. Off. | 514/213 |
| 291969 | 5/1988 | European Pat. Off. | 514/213 |
| 324377 | 1/1989 | European Pat. Off. | 514/213 |

OTHER PUBLICATIONS

Jones, et al J. Chem. Soc. pp. 2176–2181 (1969).
Davis, et al. Arch. Biochem. Biophys 102. pp. 48–51 (1963).
Wattley, et al J. Med. Chem. 28, pp. 1511–1516.
Slade, et al. J. Med. Chem 28, pp. 1517–1521 (1985).
Ott, Arch. Pharm. (Weinheim. Gen) 325 (9) pp. 601–603 (1990).
Huang, et al. Synthesis 10 p. 851 (1984).
Stewart, Australia J. Chem. 33 pp. 633–640 (1980).
Still, et al J. Org. Chem. 43 p. 2923 (1978).

Primary Examiner—Robert T. Bond
Attorney, Agent, or Firm—J. Eric Thies; David L. Rose

[57] ABSTRACT

There are disclosed certain novel compounds identified as heterocyclic-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such heterocyclic-fused lactams as the active ingredient thereof are also disclosed.

6 Claims, No Drawings

HETEROCYCLIC-FUSED LACTAMS PROMOTE RELEASE OF GROWTH HORMONE

This application is a division of application Ser. No. 08/166,440, filed Dec. 14, 1993 now U.S. Pat. No. 5,606,054.

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;

2. Decreased rate of carbohydrate utilization in cells of the body;

3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain heterocyclic-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the heterocyclic-fused lactam compounds. It is a further object of this invention to describe procedures for the preparation of such compounds. A still further object is to describe the use of such compounds to increase the secretion of growth hormone in humans and animals. A still further object of this invention is to describe compositions containing the heterocyclic-fused lactam compounds for the use of treating humans and animals so as to increase the level of growth hormone secretions. Further objects will become apparent from a reading of the following description.

DESCRIPTION OF THE INVENTION

The novel heterocyclic-fused lactams of the instant invention are best described in the following structural formula I:

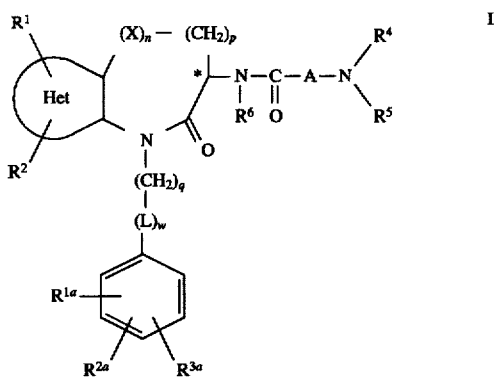

L is

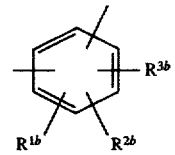

n is 0 or 1;
p is 0 to 3;
q is 0 to 4;
w is 0 or 1;
X is C=O, O, S(O)$_m$.

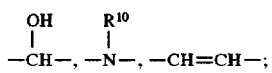

m is 0 to 2;

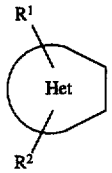

is an $R^1$, $R^2$ independently disubstituted five- or six-membered heterocycle containing from one to three heteroatoms selected from nitrogen, oxygen or sulfur; where $R^1$, $R^2$ are as defined below;

$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $C_1$–$C_3$ perfluoroalkoxy, —S(O)$_m$R$^{7a}$, cyano, nitro, $R^{7b}$O(CH$_2$)$_v$—, $R^{7b}$COO(CH$_2$)$_v$—, $R^{7b}$OCO(CH$_2$)$_v$—, $R^{5b}R^{12b}$N(CH$_2$)$_v$—, $R^{5b}R^{12b}$NCO(CH$_2$)$_v$—, phenyl or substituted phenyl where the substituents are from 1 to 3 of halogen, $C_1$–$C_6$ alkyl, $C_1$–$C_6$ alkoxy, or hydroxy; v is 0 to 3 and m is 0 to 2;

$R^{7a}$ and $R^{7b}$ are independently hydrogen, $C_1$–$C_3$ perfluoroalkyl, $C_1$–$C_6$ alkyl, substituted $C_1$–$C_6$ alkyl where the substitutents are phenyl or substituted phenyl; phenyl or substituted phenyl where the phenyl substitutents are from 1 to 3 of halogen, $C_1$–$C_6$ alkyl, $C_1$–$C_6$ alkoxy or hydroxy;

$R^{3a}$ and $R^{3b}$ are independently hydrogen, $R^9$, $C_1$–$C_6$ alkyl substituted with $R^9$, phenyl substituted with $R^9$ or phenoxy substituted with $R^9$;

$R^9$ is

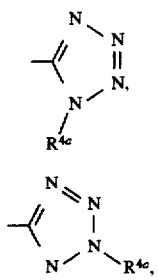

$R^{7b}$O(CH$_2$)$_v$—, $R^{7b}$COO(CH$_2$)$_v$—, $R^{7b}$OCO(CH$_2$)$_v$—, $R^{7b}$CO(CH$_2$)$_v$—, $R^{7b}$O(CH$_2$)CO—, $R^{5b}R^{12b}$N(CH$_2$)$_v$—, $R^{5b}R^{12b}$NCO(CH$_2$)$_v$—, $R^{5b}R^{12b}$NCS(CH$_2$)$_v$—, $R^{5b}R^{12c}$NN(R$^{12b}$)CO(CH$_2$)$_v$—, $R^{5b}R^{12c}$NN(R$^{12b}$)CS(CH$_2$)$_v$—, $R^{5b}R^{12b}$NCON(R$^{12a}$)(CH$_2$)$_v$—, $R^{5b}R^{12b}$NCSN(R$^{12a}$)(CH$_2$)$_v$—, $R^{5b}R^{12c}$NN(R$^{12b}$)CSN(R$^{12a}$)(CH$_2$)$_v$—, $R^{5b}R^{12c}$NN(R$^{12b}$)CON(R$^{12a}$)(CH$_2$)$_v$—, $R^{5b}R^{12c}$NN(R$^{12b}$)COO(CH$_2$)$_v$—, $R^{5b}R^{12b}$NCOO(CH$_2$)$_v$— or $R^{13}$OCON(R$^{12a}$)(CH$_2$)$_v$—, where v is 0 to 3;

$R^{12a}$, $R^{12b}$ and $R^{12c}$ are independently $R^{5a}$, OR$^{5a}$ or COR$^{5a}$, $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$–$C_3$ perfluoroalkyl, $C_1$–$C_6$ alkyl, substituted $C_1$–$C_6$ alkyl, where the substitutents are hydroxy, —NR$^{10}$R$^{11}$, carboxy, phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy;

$R^{10}$ and $R^{11}$ are independently hydrogen, $C_1$–$C_6$ alkyl, phenyl, phenyl $C_1$–$C_6$ alkyl, $C_1$–$C_5$ alkoxycarbonyl or $C_1$–$C_5$ alkanoyl-$C_1$–$C_6$ alkyl;

$R^4$, $R^{4a}$, $R^5$, $R^{5a}$ and $R^{5b}$ are independently hydrogen, phenyl, substituted phenyl, $C_1$–$C_{10}$ alkyl, substituted $C_1$–$C_{10}$ alkyl, $C_3$–$C_{10}$ halkenyl, substituted $C_3$–$C_{10}$ alkenyl, $C_3$–$C_{10}$ alkynyl or substituted $C_3$–$C_{10}$ alkynyl where the substituents on the phenyl, alkyl, alkenyl or alkynyl are from 1 to 5 of hydroxy, $C_1$–$C_6$ alkoxy, $C_3$–$C_7$ cycloalkyl, fluoro, $R^1$, $R^2$ independently disubstituted phenyl, $R^1$, $R^2$ independently disubstituted phenyl $C_1$–$C_3$ alkoxy, $C_1$–$C_{20}$-alkanoyloxy, $C_1$–$C_5$ alkoxycarbonyl, carboxy, formyl or —NR$^{10}$R$^{11}$ where $R^1$, $R^2$, $R^{10}$ and $R^{11}$ are as defined above; or $R^4$ and $R^5$ can be taken together to form —(CH$_2$)$_r$—B—(CH$_2$)$_s$— where B is CHR$^1$, O, S(O)$_m$ or N—R$^{10}$, r and s are independently 1 to 3, m is 0, 1 or 2 and $R^1$ and $R^{10}$ are as defined above;

$R^6$ is hydrogen, $C_1$–$C_{10}$ alkyl, phenyl or phenyl $C_1$–$C_{10}$ alkyl;

A is

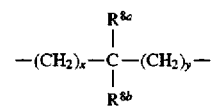

where x and y are independently 0–3;

$R^{8a}$ and $R^{8b}$ are independently hydrogen, $C_1$–$C_{10}$ alkyl, trifluoromethyl, $R^1$, $R^2$ independently disubstituted phenyl, substituted $C_1$–$C_{10}$ alkyl where the substitutents are from 1 to 3 of imidazolyl, indolyl, hydroxy, fluoro, —S(O)$_m$R$^{7a}$, $C_1$–$C_6$ alkoxy, $C_3$–$C_7$ cycloalkyl, $R^1$, $R^2$ independently disubstituted phenyl, $R^1$, $R^2$ independently disubstituted phenyl $C_1$–$C_3$ alkoxy, $C_1$–$C_5$ alkanoyloxy, $C_1$–$C_5$ alkoxycarbonyl, carboxy, formyl or —NR$^{10}$R$^{11}$ where $R^1$, $R^2$, $R^{7a}$, $R^{10}$, $R^{11}$ and m are as defined above; or $R^{8a}$ and $R^{8b}$ can be taken together to form —(CH$_2$)$_t$— where t is 2 to 6; and $R^{8a}$ and $R^{8b}$ can independently be joined to one or both of $R^4$ and $R^5$ to form alkylene bridges between the terminal nitrogen and the alkyl portion of the A group wherein the bridge contains from one to five carbon atoms; and pharmaceutically acceptable salts thereof.

In the above structural formula and throughout the instant specification, the following terms have the indicated meanings:

Heterocycles described by formula I include, but are not limited to: pyrrole, furan, thiophene, imidazole, pyrazole, oxazole, thiazole, triazole, pyridine, pyridazine, pyrazine and pyrimidine.

It is intended that the lactam portion of Formula I be fused to the heterocycle at any two adjacent atoms of the heterocycle such that the heteroatoms are at any position of the Het group and that one or two of the nitrogen heteroatoms can be at the bridgehead positions (the positions shared by both Het and the lactam ring). In addition, one or more unsaturations may be present in the Het group. It should be noted that all positional isomers with the heteroatoms taking various in the Het group are included within the scope of this invention.

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;

p is 0 to 3;

q is 0 to 2;
w is 0 or 1;
X is O, S(O)$_m$,

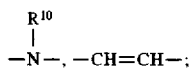

m is 0 to 2;

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl where the substitutents are phenyl; phenyl and v is 0 to 3;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is

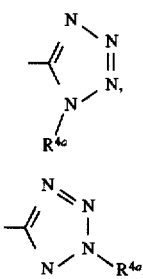

R$^{7b}$O(CH$_2$)$_v$—, R$^{7b}$COO(CH$_2$)$_v$—, R$^{7b}$OCO(CH$_2$)$_v$—,
R$^{7b}$CO(CH$_2$)$_v$—, R$^{5b}$R$^{12b}$N(CH$_2$)$_v$—,
R$^{5b}$R$^{12b}$NCO(CH$_2$)$_v$—, R$^{5b}$R$^{12b}$NCS(CH$_2$)$_v$—,
R$^{5b}$R$^{12c}$NN(R$^{12b}$)CO(CH$_2$)$_v$—,
R$^{5b}$R$^{12b}$NCON(R$^{12a}$)(CH$_2$)$_v$—,
R$^{5b}$R$^{12c}$NCSN(R$^{12a}$)(CH$_2$)$_v$—,
R$^{5b}$R$^{12c}$NN(R$^{12b}$)CSN(R$^{12a}$)(CH$_2$)$_v$—,
R$^{5b}$R$^{12c}$NN(R$^{12b}$)CON(R$^{12a}$)(CH$_2$)$_v$—,
R$^{5b}$R$^{12c}$NN(R$^{12b}$)COO(CH$_2$)$_v$—, R$^{5b}$R$^{12b}$NCOO(CH$_2$)$_v$— or R$^{13}$OCON(R$^{12a}$)(CH$_2$)$_v$—, and v is 0 to 3;

$R^{12a}$, $R^{12b}$ and $R^{12c}$ are independently $R^{5a}$, OR$^{5a}$ or COR$^{5a}$, $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substitutents are hydroxy, —NR$^{10}$R$^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^{10}$ and $R^{11}$ are independently hydrogen, $C_1$-$C_6$ alkyl, phenyl $C_1$-$C_6$ alkyl, or $C_1$-$C_5$ alkanoyl-$C_1$-$C_6$ alkyl;

$R^4$, $R^{4a}$, $R^5$, $R^{5a}$ and $R^{5b}$ are independently hydrogen, phenyl, substituted phenyl, $C_1$-$C_{10}$ alkyl, substituted $C_1$-$C_{10}$ alkyl where the substituents on the alkyl or phenyl are from 1 to 5 of hydroxy, $C_1$-$C_6$ alkoxy, $C_3$-$C_7$ cycloalkyl, fluoro, $R^1$, $R^2$ independently disubstituted phenyl, $R^1$, $R^2$ independently disubstituted phenyl $C_1$-$C_3$ alkoxy, $C_1$-$C_{20}$-alkanoyloxy, $C_1$-$C_5$ alkoxycarbonyl, carboxy or formyl; $R^4$ and $R^5$ can be taken together to form —(CH$_2$)$_r$—B—CH$_2$)$_s$— where B is CHR$^1$, O, S(O)$_m$ or N—R$^{10}$, r and s are independently 1 to 3, m is 0, 1 or 2 and $R^1$ and $R^{10}$ are as defined above;

$R^6$ is hydrogen, $C_1$-$C_{10}$ alkyl or phenyl $C_1$-$C_{10}$ alkyl;

A is

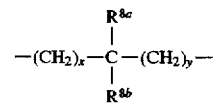

where x and y are independently 0-2;

$R^{8a}$ and $R^{8b}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —S(O)$_m$R$^{7a}$, $C_1$-$C_6$ alkoxy, $C_3$-$C_7$ cycloalkyl, $R^1$, $R^2$ independently disubstituted phenyl, $R^1$, $R^2$ independently disubstituted phenyl $C_1$-$C_3$ alkoxy, $C_1$-$C_5$ alkanoyloxy, $C_1$-$C_5$ alkoxycarbonyl, carboxy, formyl or —NR$^{10}$R$^{11}$ where $R^1$, $R^2$, $R^{7a}$, $R^{10}$, $R^1$ and m are as defined above; or $R^{8a}$ and $R^{8b}$ can be taken together to form —(CH$_2$)$_t$— where t is 2 to 4; and $R^{8a}$ and $R^{8b}$ can independently be joined to $R^5$ to form alkylene bridges between the terminal nitrogen and the alkyl portion of the A group wherein the bridge contains from one to five carbon atoms;

and pharmaceutically acceptable salts thereof.

Additional preferred compounds are realized in the above structural formula when:

n is 0 or 1;
p is 0 to 2;
q is 0 to 2;
w is 0 or 1;
X is S(O)$_m$ or —CH═CH—;
m is 0 or 1;

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl
where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl or substituted $C_1$-$C_6$ alkyl where the substituents are phenyl and v is 0 to 2;

$R^{3a}$ and $R^{3b}$ are independently hydrogen, $R^9$, $C_1$-$C_6$ alkyl substituted with $R^9$ or phenoxy substituted with $R^9$;

$R^9$ is

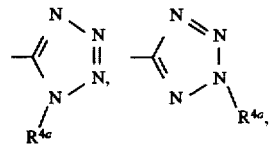

R$^{7b}$O(CH$_2$)$_v$—, R$^{7b}$COO(CH$_2$)$_v$—, R$^{7b}$OCO(CH$_2$)$_v$—,
R$^{7b}$CO(CH$_2$)$_v$—, R$^{5b}$R$^{12b}$N(CH$_2$)$_v$—,
R$^{5b}$R$^{12b}$NCO(CH$_2$)$_v$—, R$^{5b}$R$^{12c}$N(R$^{12b}$)CO(CH$_2$)$_v$—,
R$^{5b}$R$^{12b}$NCON(R$^{12a}$)(CH$_2$)$_v$—,
R$^{5b}$R$^{12c}$NN(R$^{12b}$)CSN(R$^{2a}$)(CH$_2$)$_v$—,
R$^{5b}$R$^{12c}$NN(R$^{12b}$)CON(R$^{2a}$)(CH$_2$)$_v$—,
R$^{5b}$R$^{12c}$NN(R$^{12b}$)COO(CH$_2$)$_v$—, R$^{5b}$R$^{12b}$NCOO(CH$_2$)$_v$— or R$^{13}$OCON(R$^{12a}$)(CH$_2$)$_v$—, where v is 0 to 2;

$R^{12a}$, $R^{12b}$ and $R^{12c}$ are independently $R^{5a}$ or $OR^{5a}$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;

$R^{13}$ is $C_1-C_6$ alkyl, substituted $C_1-C_6$ alkyl, where the substitutents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^{10}$ and $R^{11}$ are independently hydrogen, $C_1-C_6$ alkyl, phenyl $C_1-C_6$ alkyl, or $C_1-C_5$ alkanoyl-$C_1-C_6$ alkyl;

$R^4$, $R^{4a}$, $R^5$, $R^{5a}$ and $R^{5b}$ are independently hydrogen, $C_1-C_{10}$ alkyl or substituted $C_1-C_{10}$ alkyl where the substituents are from 1 to 5 of hydroxy, $C_1-C_6$ alkoxy, fluoro, $R^1$, $R^2$ independently disubstituted phenyl, $C_1-C_{20}$-alkanoyloxy, $C_1-C_5$ alkoxycarbonyl or carboxy; where $R^1$ and $R^2$ are as defined above;

$R^6$ is hydrogen or $C_1-C_{10}$ alkyl;

A is

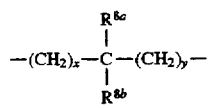

where x and y are independently 0-1;

$R^{8a}$ and $R^{8b}$ are independently hydrogen, $C_1-C_{10}$ alkyl, substituted $C_1-C_{10}$ alkyl where the substitutents are from 1 to 3 of imidazolyl, indolyl, hydroxy, fluoro, $S(O)_mR^{7a}$, $C_1-C_6$ alkoxy, $C_3-C_7$ cycloalkyl, $R^1$, $R^2$ independently disubstituted phenyl, $R^1$, $R^2$ independently disubstituted phenyl $C_1-C_3$ alkoxy, $C_1-C_5$ alkanoyloxy, $C_1-C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^{8a}$ and $R^{8b}$ can be taken together to form —$(CH_2)_t$— where t is 2; and $R^{8a}$ and $R^{8b}$ can independently be joined to $R^5$ to form alkylene bridges between the terminal nitrogen and the alkyl portion of the A group wherein the bridge contains from one to five carbon atoms;

and pharmaceutically acceptable salts thereof.

Still further preferred compounds of the instant invention are realized in the above structural formula when;

n is 0 or 1;

p is 0 to 2;

q is 1;

w is 1;

X is $S(O)_m$ or —CH=CH—;

m is 0 or 1;

$R^1$, $R^2$, $R^{1a}$, $R^{2a}$, $R^{1b}$ and $R^{2b}$ are independently hydrogen, halogen, $C_1-C_7$ alkyl, $C_1-C_3$ perfluoroalkyl, $S(O)_m$ $R^{7a}$, $R^{7b}O(CH_2)_v$—, $R^{7b}COO(CH_2)_v$—, phenyl or substituted phenyl where the substituents are from 1 to 3 of halogen, $C_1-C_6$ alkyl, $C_1-C_6$ alkoxy, or hydroxy;

$R^{7a}$ and $R^{7b}$ are independently hydrogen, $C_1-C_6$ alkyl or substituted $C_1-C_6$ alkyl where the substitutents are phenyl and v is 0 or 1;

$R^{3a}$ and $R^{3b}$ are independently hydrogen, $R^9$ or $C_1-C_6$ alkyl substituted with $R^9$;

$R^9$ is

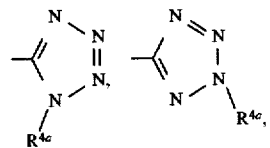

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—, $R^{5b}R^{12b}NCO(CH_2)_v$—, $R^{5b}R^{12c}NN(R^{12b})CO(CH_2)_v$—, $R^{5b}R^{12b}NCON(R^{12a})(CH_2)_v$—, $R^{5b}R^{12c}NN(R^{12b})CON(R^{12a})(CH_2)_v$—, $R^{5b}R^{12c}NN(R^{12b})COO(CH_2)_v$—, $R^{5b}R^{12b}NCOO(CH_2)_v$—, or $R^{13}OCON(R^{12a})(CH_2)_v$—, where v is 0 to 2;

$R^{12a}$, $R^{12b}$ and $R^{12c}$ are independently $R^5a$, $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;

$R^{13}$ is $C_1-C_6$ alkyl, substituted $C_1-C_6$ alkyl, where the substitutents are phenyl or substituted phenyl; phenyl or substituted phenyl where the substituents on the phenyl are from 1 to 3 of halogen, $C_1-C_6$ alkyl, $C_1-C_6$ alkoxy or hydroxy;

$R^{10}$ and $R^{11}$ are independently hydrogen, $C_1-C_6$ alkyl or $C_1-C_5$ alkanoyl-$C_1-C_6$ alkyl;

$R^4$, $R^{4a}$, $R^5$, $R^{5a}$ and $R^{5b}$ are independently hydrogen, $C_1-C_{10}$ alkyl or substituted $C_1-C_{10}$ alkyl where the substituents are from 1 to 3 of hydroxy, $C_1-C_3$ alkoxy, fluoro, $R^1$, $R^2$ independently disubstituted phenyl, $C_1-C_{20}$-alkanoyloxy, $C_1-C_5$ alkoxycarbonyl or carboxy; where $R^1$ and $R^2$ are as defined above;

$R^6$ is hydrogen;

A is

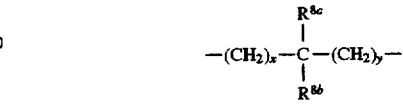

where x and y are independently 0 or 1;

$R^{8a}$ and $R^{8b}$ are independently hydrogen, $C_1-C_{10}$ alkyl, substituted $C_1-C_{10}$ alkyl where the substituents are from 1 to 3 of imidazolyl, indolyl, hydroxy, fluoro, $S(O)_mR^{7a}$, $C_1-C_6$ alkoxy, $C_3-C_7$ cycloalkyl, $R^1$, $R^2$ independently disubstituted phenyl, $C_1-C_5$ alkanoyloxy, $C_1-C_5$ alkoxycarbonyl or carboxy, where $R^1$, $R^2$, $R^{7a}$, and m are as defined; or $R^{8a}$ and $R^{8b}$ can be taken together to form —$(CH_2)_t$— where t is 2; and $R^{8a}$ and $R^{8b}$ can independently be joined to $R^5$ to form alkylene bridges between the terminal nitrogen and the alkyl portion of the A group wherein the bridge contains from one to five carbon atoms; and pharmaceutically acceptable salts thereof.

Representative preferred growth hormone releasing compounds of the present invention include the following:

1. 3-Amino-3-methyl-N-[6,7,8,9-tetrahydro-8-oxo-9-[[2'-(1H-tetrazol-5-yl)[1,1'-biphenyl]-4-yl]methyl]-5H-pyrido[2,3-b]-azepin-7(R)-yl]butanamide;

2. N-Ethyl-4'-[[7(R)-[[3-amino-3-methyl-1-oxobutyl]amino]-6,7,8,9-tetrahydro-8-oxo-5H-pyrido[2,3-b]azepin-9-yl]-methyl][1,1'-biphenyl]-2-carboxamide;

3. 3-Amino-3-methyl-N-[6,7,8,9-tetrahydro-8-oxo-9-[[2'-[(methylamino)carbonyl]amino][1,1'-biphenyl]4-yl]-methyl]-5H-pyrido[2,3-b]azepin-7(R)-yl]butanamide;

4. 3-Amino-3-methyl-N-[6,7,8,9-tetrahydro-8-oxo-9-[[2'-[[[(methylamino)carbonyl]amino]methyl][1,1'-biphenyl]-4-yl]methyl]-5H-pyrido[2,3-b]azepin-7(R)-yl]butanamide;

5. 3-Amino-N-[5,6,7,8-tetrahydro-5-oxo-4-[[2'-(1H-tetrazol-5-yl)[1,1'-biphenyl]4-yl]methyl]-4H-thieno[3,2-b]azepin-6(R)-yl]-3-methylbutanamide 6. N-Ethyl-4'-[[6(R)-[[3-amino-3-methyl-1-oxobutyl]amino]-5,6,7,8-tetrahydro-5-oxo-4H-thieno[3,2-b]azepin-4-yl]-methyl][1,1'-biphenyl]-2-carboxamide;

7. 3-Amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-3-methylbutanamide;

8. 3-Amino-3-methyl-N-[6,7,8,9-tetrahydro-8-oxo-9-[[2'-[[[(methylamino)carbonyl]amino]methyl][1,1'-biphenyl]-4-yl]methyl]-5H-pyrido[2,3-b]azepin-7(R)-yl]butanamide;

9. N-[1,4,5,6,7,8-Hexahydro-5-oxo-4-[[2'-(1H-tetrazol-5-yl)-[1,1'-biphenyl]-4-yl]methyl]pyrrolo[3,2-b]azepin-6(R)-yl]-3-amino-3-methylbutanamide;

10. N-Ethyl-4'-[[6(R)-[[3-amino-3-methyl-1-oxobutyl]amino]-1,4,5,6,7,8-hexahydro-5-oxo-pyrrolo[3,2-b]azepin-4-yl]-methyl][1,1'-biphenyl]-2-carboxamide;

11. N-[1,4,5,6,7,8-Hexahydro-5-oxo-4-[[2'-[[(methylamino)carbonyl]amino][1,1'-biphenyl]-4-yl]methyl]pyrrolo[3,2-b]azepin-6(R)-yl]-3-amino-3-methylbutanamide;

12. N-[1,4,5,6,7,8-Hexahydro-5-oxo-4-[[2'-[[[(methylamino)carbonyl]amino]methyl][1,1'- biphenyl]-4-yl]methyl]pyrrolo[3,2-b]azepin-6(R)-yl]-3-amino-3-methylbutanamide;

13. 3-[2(R)-Hydroxypropyl]amino-3-methyl-N-[6,7,8,9-tetrahydro-8-oxo-9-[[2'-(1H-tetrazol-5-yl)[1,1'-biphenyl]-4-yl]-methyl]-5H-pyrido[2,3-b]azepin-7(R)-yl]butanamide;

14. N-Ethyl-4'-[[7(R)-[[3-[2(R)-hydroxypropyl]amino-3-methyl-1-oxobutyl]amino]-6,7,8,9-tetrahydro-8-oxo-5H-pyrido[2,3-b]azepin-9-yl]methyl][1,1'-biphenyl]-2-carboxamide;

15. 3-[2(R)-Hydroxypropyl]amino-3-methyl-N-[6,7,8,9-tetrahydro-8-oxo-9-[[2'-[[(methylamino)carbonyl]amino][1,1'-biphenyl]-4-yl]methyl]-5H-pyrido[2,3-b]azepin-7(R)-yl]-butanamide;

16. 3-[2(R)-Hydroxypropyl]amino-3-methyl-N-[6,7,8,9-tetrahydro-8-oxo-9-[[2'-[[[(methylamino)carbonyl]amino]methyl][1,1'-biphenyl]-4-yl]methyl]-5H-pyrido[2,3-b]-azepin-7(R)-yl]butanamide;

17. 3-[2(R)-Hydroxypropyl]amino-N-[5,6,7,8-tetrahydro-5-oxo-4-[[2'-(1H-tetrazol-5-yl) [1,1'-biphenyl]-4-yl]methyl]-4H-thieno[3,2-b]azepin-6(R)-yl]-3-methylbutanamide 18. N-Ethyl-4'-[[6(R)-[[3-[2(R)-hydroxypropyl]amino-3-methyl-1-oxobutyl]amino]-5,6,7,8-tetrahydro-5-oxo-4H-thieno[3,2-b]azepin-4-yl]methyl][1,1'-biphenyl]-2-carboxamide;

19. 3-[2(R)-Hydroxypropyl]amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-3-methylbutanamide;

20. 3-[2(R)-Hydroxypropyl]amino-3-methyl-N-[6,7,8,9-tetrahydro-8-oxo-9-[[2'-[[[(methylamino)carbonyl]amino]methyl][1,1'-biphenyl]-4-yl]methyl]-5H-pyrido[2,3-b]azepin-7(R)-yl]butanamide;

21. N-[1,4,5,6,7,8-Hexahydro-5-oxo-4-[[2'-(1H-tetrazol-5-yl)-[1,1'-biphenyl]-4-yl]methyl]pyrrolo[3,2-b]azepin-6(R)-yl]-3-[2(R)-hydroxypropyl]amino-3-methylbutanamide;

22. N-Ethyl-4'-[[6(R)-[[3-[2(R)-hydroxypropyl]amino-3-methyl-1-oxobutyl]amino]-1,4,5,6,7,8-hexahydro-5-oxopyrrolo[3,2-b]azepin-4-yl]methyl][1,1'-biphenyl]-2-carboxamide;

23. N-[1,4,5,6,7,8-Hexahydro-5-oxo-4-[[2'-[[(methylamino)carbonyl]amino][1,1'-biphenyl]-4-yl]methyl]pyrrolo[3,2-b]azepin-6(R)-yl]-3-[2(R)-hydroxypropyl]amino-3-methylbutanamide;

24. N-[1,4,5,6,7,8-Hexahydro-5-oxo-4-[[2'-[[[(methylamino)carbonyl]amino]methyl][1,1'- biphenyl]-4-yl]methyl]pyrrolo[3,2-b]azepin-6(R)-yl]-3-[2(R)-hydroxypropyl]amino-3-methylbutanamide;

25. 3-[2(S),3-Dihydroxypropyl]amino-3-methyl-N-[6,7,8,9-tetrahydro-8-oxo-9-[[2'-(1 H-tetrazol-5-yl)[1,1'-biphenyl]-4-yl]methyl]-5H-pyrido[2,3-b]azepin-7(R)-yl]butanamide;

26. N-Ethyl-4'-[[7(R)-[[3-[2(S),3-dihydroxypropyl]amino-3-methyl-1-oxobutyl]amino]-6,7,8,9-tetrahydro-8-oxo-5H-pyrido[2,3-b]azepin-9-yl]methyl][1,1'-biphenyl]-2-carboxamide;

27. 3-[2(S),3-Dihydroxypropyl]amino-3-methyl-N-[6,7,8,9-tetrahydro-8-oxo-9-[[2'-[[(methylamino)carbonyl]amino]-[1,1'-biphenyl]-4-yl]methyl]-5H-pyrido[2,3-b]azepin-7(R)-yl]butanamide;

28. 3-[2(S),3-Dihydroxypropyl]amino-3-methyl-N-[6,7,8,9-tetrahydro-8-oxo-9-[[2'-[[[(methylamino)carbonyl]amino]methyl][1,1'-biphenyl]-4-yl]methyl]-5H-pyrido[2,3-b]azepin-7(R)-yl]butanamide;

29. 3-[2(S),3-Dihydroxypropyl]amino-N-[5,6,7,8-tetrahydro-5-oxo-4-[[2'-(1H-tetrazol-5-yl)[1,1'-biphenyl]-4-yl]methyl]-4H-thieno[3,2-b]azepin-6(R)-yl]-3-methylbutanamide 30. N-Ethyl-4'-[[6(R)-[[3-[2(S),3-dihydroxypropyl]amino-3-methyl-1-oxobutyl]amino]-5,6,7,8-tetrahydro-5-oxo-4H-thieno[3,2-b]azepin-4-yl]methyl][1,1'-biphenyl]-2-carboxamide;

31. 3-[2(S),3-Dihydroxypropyl]amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-3-methylbutanamide;

32. 3-[2(S),3-Dihydroxypropyl]amino-3-methyl-N-[6,7,8,9-tetrahydro-8-oxo-9-[[2'-[[[(methylamino)carbonyl]amino]methyl][1,1'-biphenyl]-4-yl]methyl]-5H-pyrido[2,3-b]azepin-7(R)-yl]butanamide;

33. N-[1,4,5,6,7,8-Hexahydro-5-oxo-4-[[2'-(1H-tetrazol-5-yl)-[1,1'-biphenyl]-4-yl]methyl]pyrrolo[3,2-b]azepin-6(R)-yl]-3-[2(S),3-dihydroxypropyl]amino-3-methylbutanamide;

34. N-Ethyl-4'-[[6(R)-[[3-[2(S),3-dihydroxypropyl]amino-3-methyl-1-oxobutyl]amino]-1,4,5,6,7,8-hexahydro-5-oxopyrrolo[3,2-b]azepin-4-yl]methyl][1,1'-biphenyl]-2-carboxamide;

35. N-[1,4,5,6,7,8-Hexahydro-5-oxo-4-[[2'-[[(methylamino)carbonyl]amino][1,1'-biphenyl]-4-yl]methyl]pyrrolo[3,2-b]azepin-6(R)-yl]-3-[2(S),3-dihydroxypropyl]amino-3-methylbutanamide;

36. N-[1,4,5,6,7,8-Hexahydro-5-oxo-4-[[2'-[[[(methylamino)carbonyl]amino]methyl][1,1'- biphenyl]-4-yl]methyl]pyrrolo[3,2-b]azepin-6(R)-yl]-3-[2(S),3-dihydroxypropyl]amino-3-methylbutanamide;

37. 2-Amino-2-methyl-N-[6,7,8,9-tetrahydro-8-oxo-9-[[2'-(1H-tetrazol-5-yl) [1,1'-biphenyl]4-yl]methyl]-5H-pyrido[2,3-b]azepin-7(R)-yl]propanamide;

38. N-Ethyl-4'-[[7(R)-[[2-amino-2-methyl-1-oxopropyl]amino]-6,7,8,9-tetrahydro-8-oxo-5H-pyrido[2,3-b]azepin-9-yl]-methyl][1,1'-biphenyl]-2-carboxamide;

39. 2-Amino-2-methyl-N-[6,7,8,9-tetrahydro-8-oxo-9-[[2'-[[(methylamino)carbonyl]amino][1,1'-biphenyl]-4-yl]-methyl]-5H-pyrido[2,3-b]azepin-7(R)-yl]propanamide;

40. 2-Amino-2-methyl-N-[6,7,8,9-tetrahydro-8-oxo-9-[[2'-[[[(methylamino)carbonyl]amino]methyl]][1,1'-biphenyl]-4-yl]methyl]-5H-pyrido[2,3-b]azepin-7(R)-yl]propanamide;

41. 2-Amino-N-[5,6,7,8-tetrahydro-5-oxo-4-[[2'-(1H-tetrazol-5-yl)[1,1'-biphenyl]-4-yl]methyl]-4H-thieno[3,2-b]azepin-6(R)-yl]-2-methylpropanamide 42. N-Ethyl-4'-[[6(R)-[[2-amino-2-methyl-1-oxopropyl]amino]-5,6,7,8-tetrahydro-5-oxo-4H-thieno[3,2-b]azepin-4-yl]-methyl][1,1'-biphenyl]-2-carboxamide;

43. 2-Amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-2-methylpropanamide;

44. 2-Amino-2-methyl-N-[6,7,8,9-tetrahydro-8-oxo-9-[[2'-[[[(methylamino)carbonyl]amino]methyl][1,1'-biphenyl]-4-yl]methyl]-5H-pyrido[2,3-b]azepin-7(R)-yl]propanamide;

45. N-[1,4,5,6,7,8-Hexahydro-5-oxo-4-[[2'-(1H-tetrazol-5-yl)-[1,1'-biphenyl]-4-yl]methyl]pyrrolo[3,2-b]azepin-6(R)-yl]-2-amino -2-methylpropanamide;

46. N-Ethyl-4'-[[6(R)-[[2-amino-2-methyl-1-oxopropyl]amino]-1,4,5,6,7,8-hexahydro-5-oxo-pyrrolo[3,2-b]azepin-4-yl]-methyl][1,1'-biphenyl]-2-carboxamide;

47. N-[1,4,5,6,7,8-Hexahydro-5-oxo-4-[[2'-[[(methylamino)carbonyl]amino][1,1'-biphenyl]-4-yl]methyl]pyrrolo[3,2-b]azepin-6(R)-yl]-2-amino-2-methylpropanamide and 48. N-[1,4,5,6,7,8-Hexahydro-5-oxo-4-[[2'-[[[(methylamino)carbonyl]amino]methyl][1,1'-biphenyl]-4-yl]methyl]pyrrolo[3,2-b]azepin-6(R)-yl]-2-amino-2-methylpropanamide.

Representative examples of the nomenclature employed are given below:

3-Amino-3-methyl-N-[6,7,8,9-tetrahydro-8-oxo-9-[[2'-(1H-tetrazol-5-yl)[1,1'-biphenyl]-4-yl]methyl]-5H-pyrido[2,3-b]azepin-7(R)-yl]butanamide

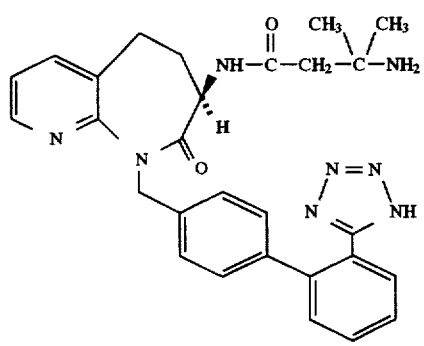

N-Ethyl-4'-[[6(R)-[[3-[2(R)-hydroxypropyl]amino-3-methyl-1-oxo-butyl]amino]-1,4,5,6,7,8-hexahydro-5-oxo-pyrrolo[3,2-b]azepin-4-yl]-methyl][1,1'-biphenyl]-2-carboxamide

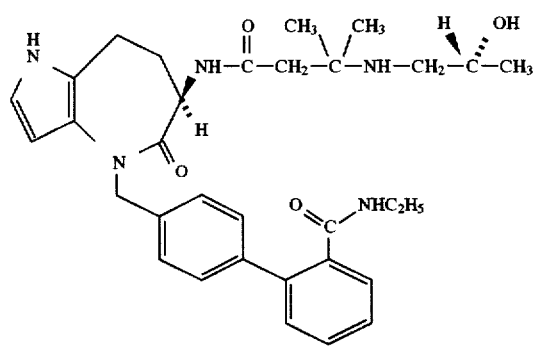

2-Amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-2-methylpropanamide

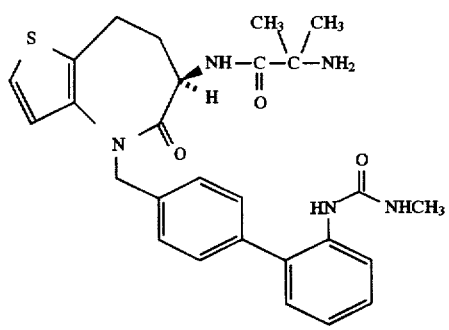

3-[2(S),3-Dihydroxypropyl]amino-3-methyl-N-[6,7,8,9-tetrahydro-8-oxo-9-[[2'-[2-[[4-morpholinocarbonyl]amino]ethyl][1,1'-biphenyl]-4-yl]-methyl]-5H-pyrido[2,3-b]azepin-7(R)-yl]butanamide

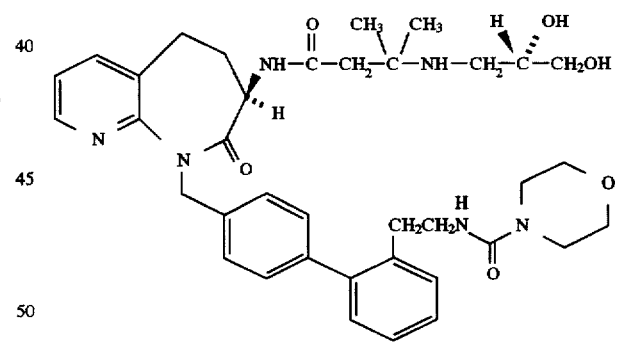

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the amino substituent adjacent to the lactam carbonyl is above the plane of the structure, as seen in Formula Ia, is more active and thus more preferred over the compound in which said substituent is below the plane of the structure. In the substituent $(X)_n$, when n=0, the asymmetric center is designated as the R-isomer. When n=1, this center will be designated according to the R/S rules as either R or S depending upon the value of X.

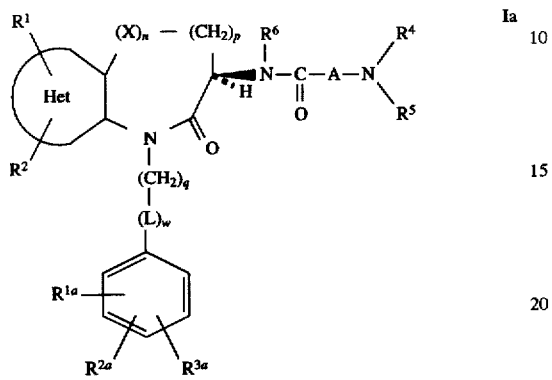

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a tetrazole or carboxy can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II. The preparation of these intermediates is described in the following reaction Schemes.

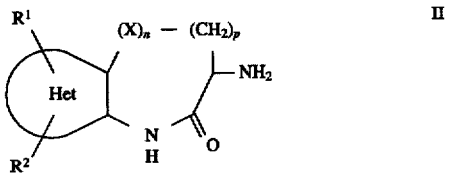

Starting with either commercially available or synthetic heterofused-cycloalkanones 1, and following the procedures described by Fisher, et al. in U.S. Pat. No. 5,206,235 and references cited therein, for the preparation of benzo-fused lactams, the corresponding oximes 2 were prepared and rearranged to the hetero-fused lactams 4 via the intermediate O-tosyl oxime 3 as shown in Scheme 1.

SCHEME 1

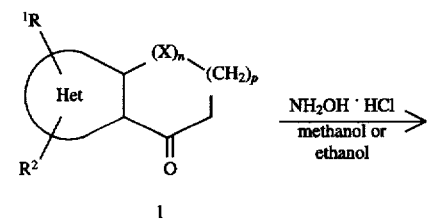

-continued
SCHEME 1

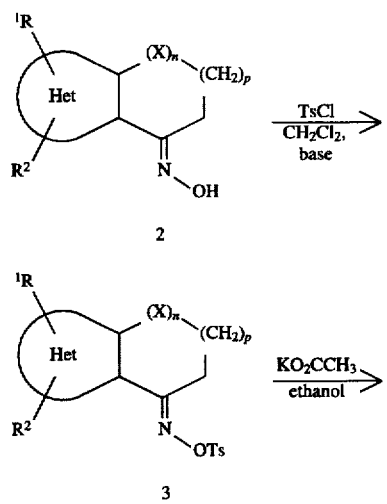

Conversion of substituted hetero-fused lactam 4 to the requisite α-amino derivative II can be achieved by a number of methods familiar to those skilled in the art, including those described for the corresponding benzo-fused lactams by Watthey, et al, *J. Med. Chem.*, 28, 1511–1516 (1985) and references cited therein. One common route proceeds via the intermediacy of an α-halo (chloro, bromo or iodo) intermediate which is subsequently displaced by a nitrogen nucleophile, typically azide. A useful method of forming the α-iodolactam intermediate 5 involves treating the hetero-fused lactam 4 with two equivalents each of iodotrimethyl-silane and iodine at low temperature, as illustrated in Scheme 2.

SCHEME 2

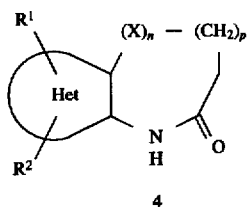

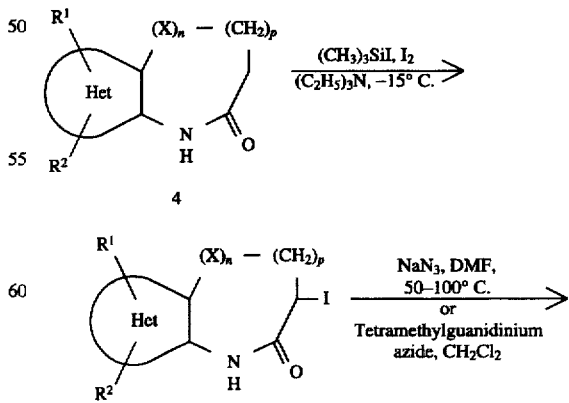

-continued
SCHEME 2

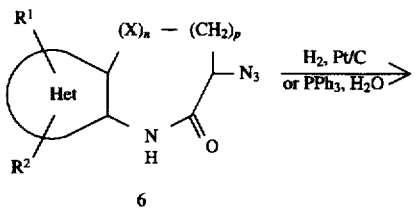

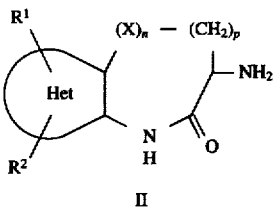

Elaboration of the iodolactam 5 to the desired α-amino lactam intermediate II is achieved by the two-step procedure illustrated in Scheme 2. Typically, iodolactam 5 is treated with sodium azide in N,N-dimethylformamide at 50°–100° C. to give the α-azido derivative 6. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative II. Formation of the α-amino derivatives of six-, seven-, eight- and nine-membered hetero-fused lactams is achieved by the routes shown in Scheme 2.

Chiral hetero-fused aminolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

Intermediates of formula II can be further elaborated to new intermediates (formula III) which are substituted on the amino group (Scheme 3). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

SCHEME 3

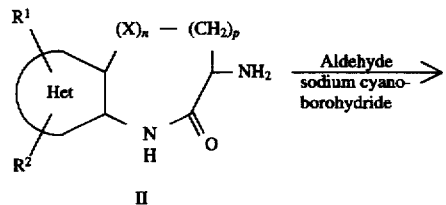

-continued
SCHEME 3

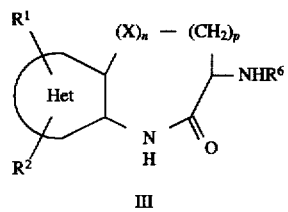

Attachment of the amino acid sidechain to intermediates of formula III is accomplished by the route shown in Scheme 4. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") or benzotriazol-1-yloxytripyrrolidinophosphonium hexafluorophosphate ("PyBOP") in an inert solvent such as methylene chloride. Separation of unwanted side products, and purification of intermediates is achieved by chromatography on silica gel, employing flash chromatography (W. C. Still, M. Kahn and A. Mitra, *J. Org. Chem.*, 43, 2923 (1978)) or by medium pressure liquid chromatography.

SCHEME 4

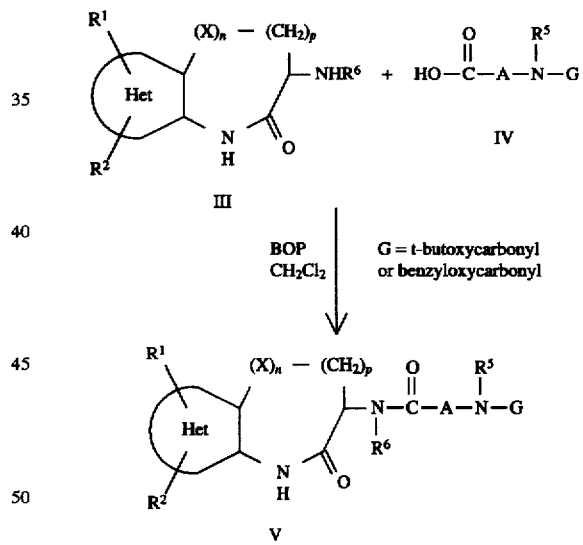

The protected amino acid derivatives IV are, in many cases, commercially available in t-butoxycarbonyl (BOC) or benzyloxycarbonyl (CBz) forms. A useful method to prepare the preferred sidechain 11 is shown in Scheme 5.

SCHEME 5

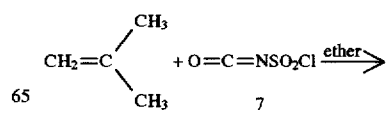

SCHEME 5

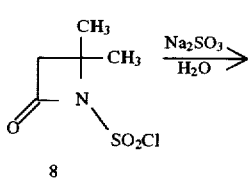
8

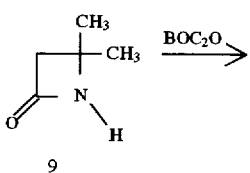
9

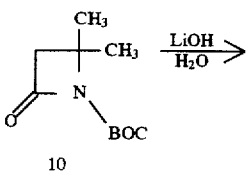
10

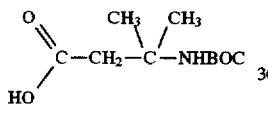
11

Reaction of isobutylene with N-chlorosulfonylisocyanate 7 in diethyl ether gives the azetidinone derivative 8. Removal of the chlorosulfonyl group with aqueous sodium sulfite followed by reaction with di-t-butyldicarbonate gives the BOC-protected intermediate 10. Alkaline hydrolysis gives the protected amino acid derivative 11 in good overall yield.

Intermediates of formula VII can be prepared as shown in Scheme 6 by treatment of the desired lactam intermediate V with an alkylating agent VI, wherein Y is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperatures of 20°–100° C. Substituents on the alkylating agent VI may need to be protected during alkylation. A description of such protecting groups may be found in: *Protective Groups in Organic Synthesis*, T. W. Greene, John Wiley and Sons, New York, 1981.

SCHEME 6

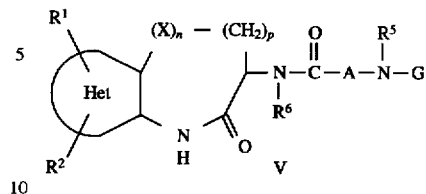
V

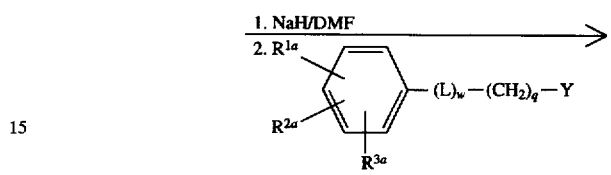
VI

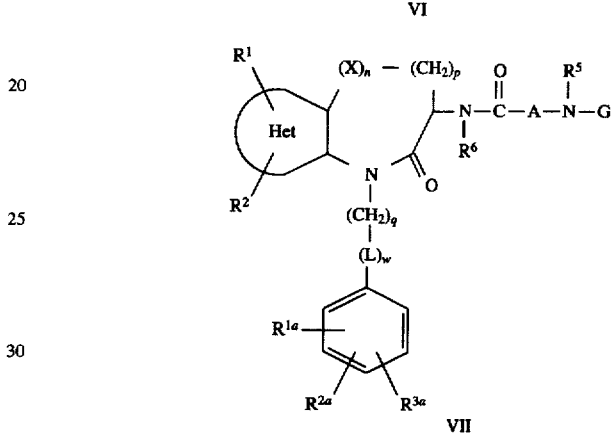
VII

Y is a leaving group
G is t-butoxycarbonyl or benzyloxycarbonyl

Alkylating agents VI are, in some cases commercially available compounds or may be prepared as described in EPO publications 253,310; 291,969; 324,377 and the references cited therein.

Compounds of formula I wherein $R^{3a}$ or $R^{3b}$ is a tetrazole are prepared as described in Scheme 7 by alkylation of V with a suitably substituted alkylating agent VI containing a nitrile as tetrazole precursor. Elaboration of nitrile 12 to the desired tetrazole product 13 is carried out by treatment with trimethyltin azide in refluxing toluene.

SCHEME 7

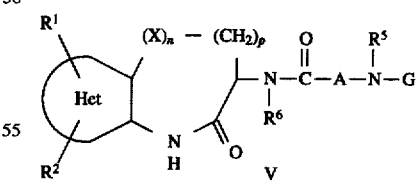
V

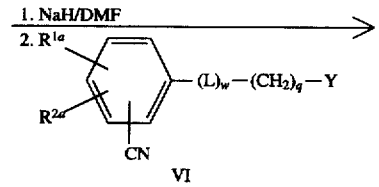
VI

SCHEME 7 -continued

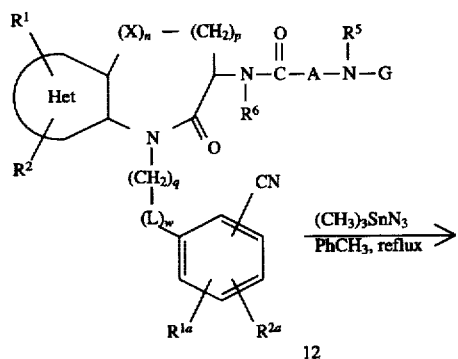

12

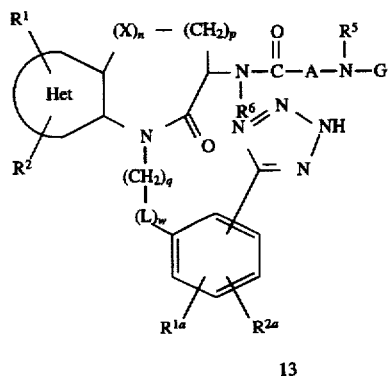

13

Y is a leaving group
G is t-butoxycarbonyl or benzyloxycarbonyl

A useful method to prepare a preferred alkylating agent 18 is shown in reaction Scheme 8, and in U.S. Pat. No. 5,039,814.

SCHEME 8

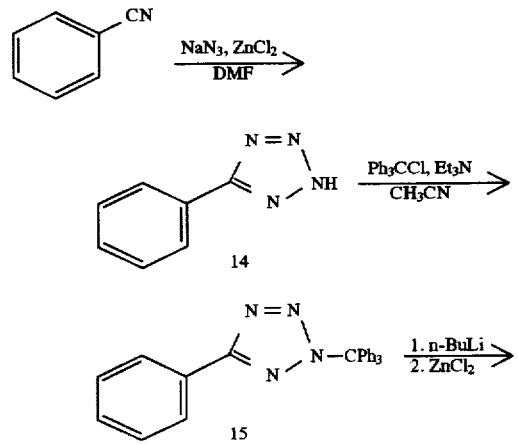

SCHEME 8 -continued

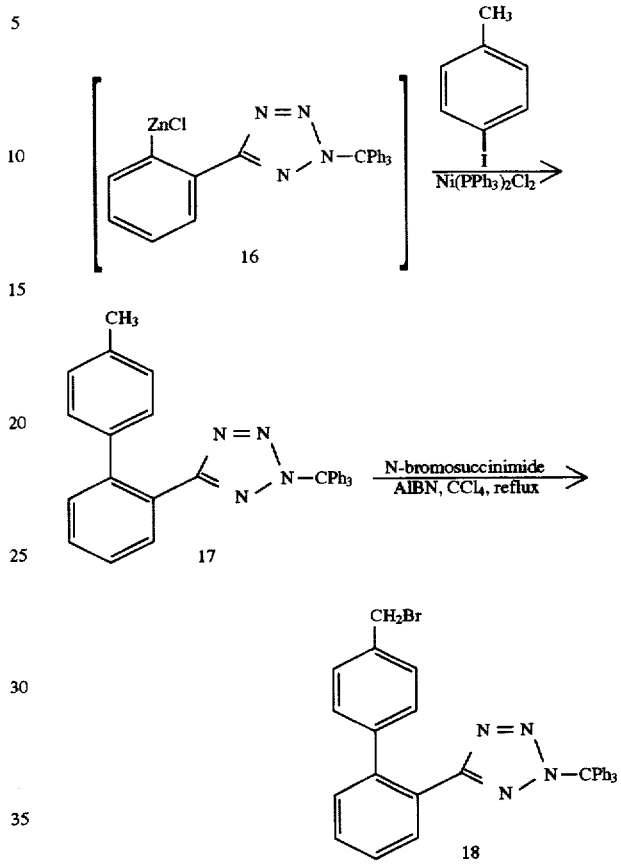

As outlined in Scheme 8, benzonitrile is treated with sodium azide and zinc chloride to give 5-phenyltetrazole 14 which is converted to the N-trityl derivative 15 by treatment with triphenylmethyl chloride and triethylamine. The zinc reagent 16 was prepared by treatment with n-butyllithium followed by zinc chloride. Coupling with 4-iodotoluene using the catalyst bis(triphenylphosphine)nickel(II) dichloride gives the biphenyl product 17 in high yield. Treatment with N-bromosuccinimide in refluxing carbon tetrachloride, in the presence of a radical initiator such as benzoyl peroxide or 2,2'-azobisisobutyronitrile (AIBN), gives bromide 18.

Intermediates of formula II where $R^{3a}$ or $R^{3b}$ is a carbamate, semicarbazide or urea derivative, wherein this functionality is attached to the phenyl ring by a nitrogen atom are prepared from intermediate 19, obtained by alkylation of V with a derivative of formula VI wherein $R^{3a}$ or $R^{3b}$ is a nitro group as shown in Scheme 9.

SCHEME 9

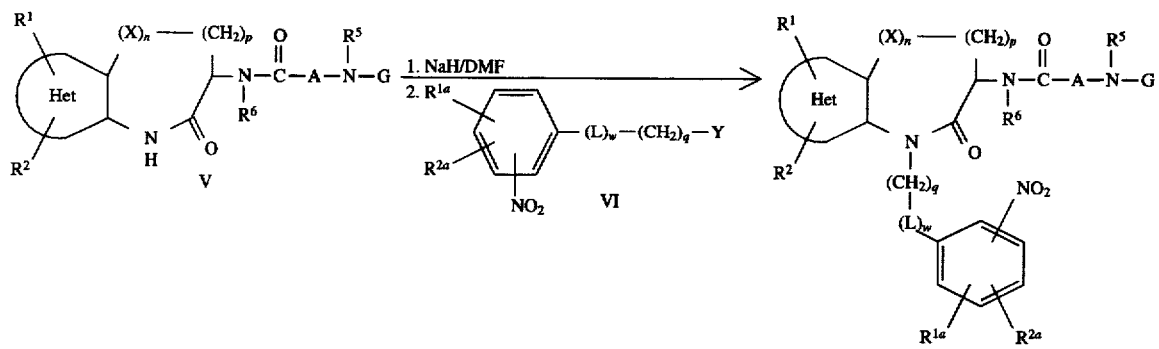

Y is a leaving group
G is t-butoxycarbonyl
or benzyloxycarbonyl

A useful method of synthesizing a preferred alkylating agent 23 is shown in reaction Scheme 10.

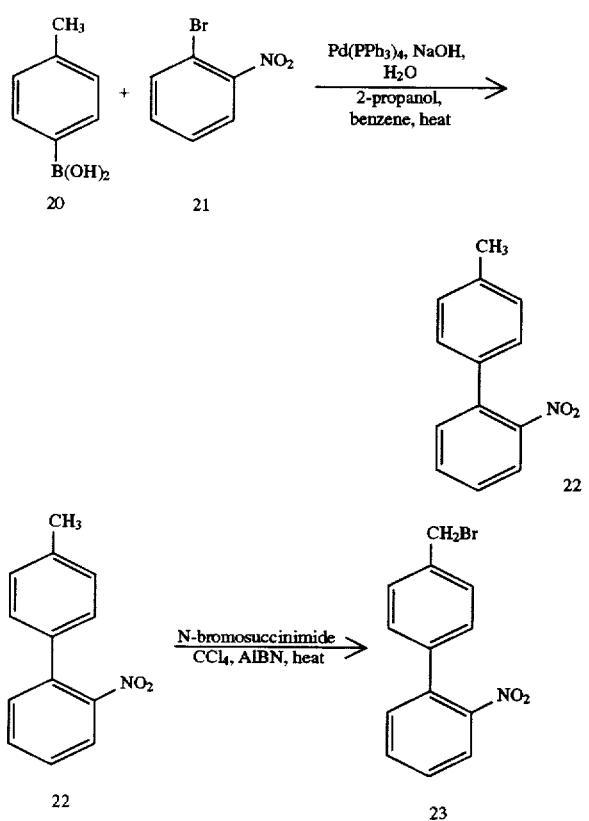

Reaction of 4-tolylboronic acid 20 with 2-bromonitrobenzene 21 in the presence of a transition metal catalyst such as tetrakis(triphenylphosphine)palladium(O) in a mixed solvent system containing aqueous sodium hydroxide, water, 2-propanol and benzene at elevated temperatures for several hours gives the coupled product 22 in good overall yield. Chromatographic purification and separation of unwanted by-products is conveniently performed on silica, eluting with common organic solvents such as hexane, ethyl acetate and methylene chloride. Conversion of 22 to the bromide derivative 23 is accomplished by the aforementioned treatment with N-bromosuccinimide.

As shown in Scheme 11, reduction of the nitro group of 19 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 19 must be compatible with the experimental conditions anticipated for reduction. For example, intermediate 19 wherein G is t-butoxycarbonyl (BOC) is stable to the conditions of catalytic reduction employed in the conversion to 24. Intermediate 24 may also be further elaborated to a new intermediate 25 by reductive alkylation carried out under the conditions described above.

SCHEME 11

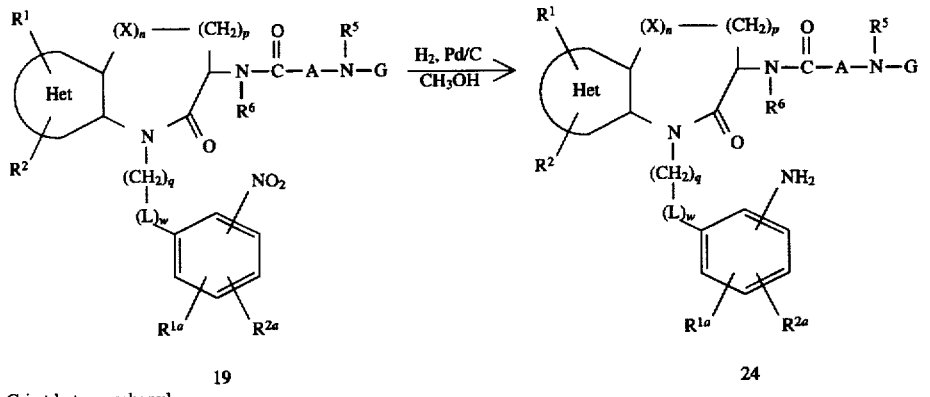

G is t-butoxycarbonyl

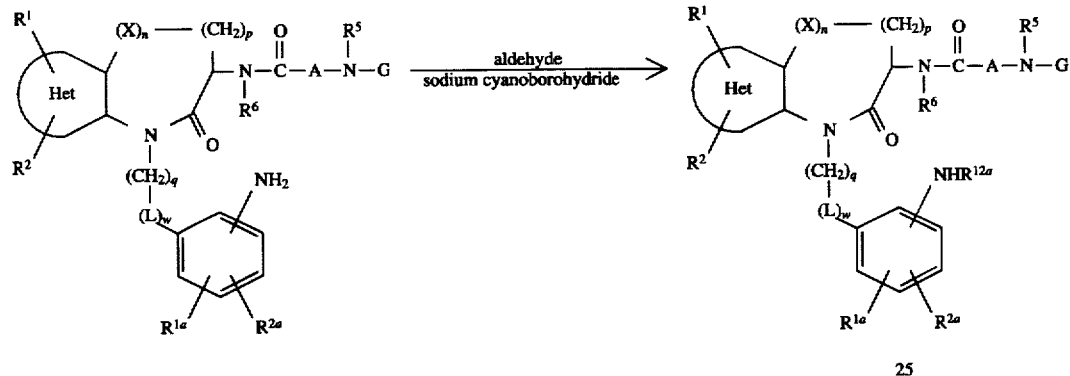

Elaboration of 25 to carbamate compound 26 is achieved by reaction with the appropriate chloroformate reagent in pyridine or in methylene chloride with triethylamine as shown in Scheme 12.

mono-substituted compound 30 wherein either $R^{5b}$ or $R^{12b}$ is hydrogen is obtained from 25 by reaction with an isocyanate 29 as shown in Scheme 13. Terminally unsubstituted urea 30, wherein $R^{12b}$ is hydrogen, is also prepared from

SCHEME 12

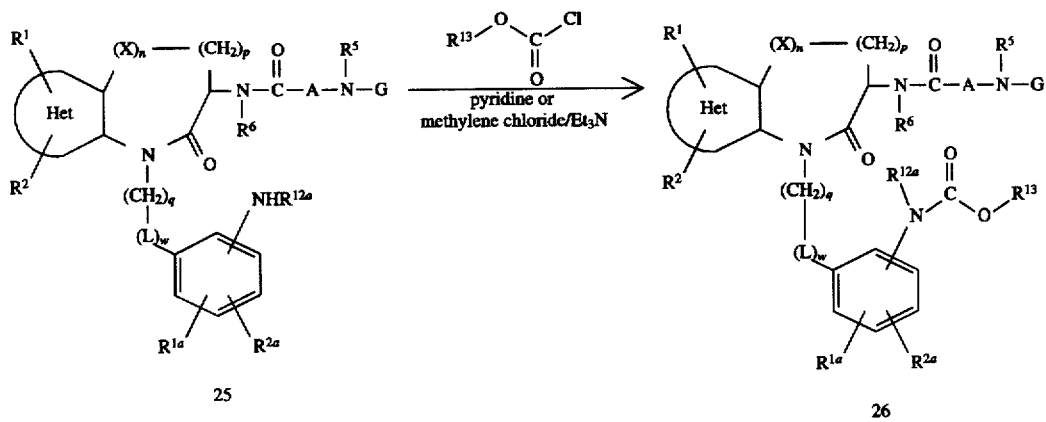

Transformation of amine intermediate 25 to urea derivatives is accomplished in several ways. Terminally disubstituted compounds 28 can be obtained directly by reaction of 25 with a disubstituted carbamoyl chloride 27 in an inert solvent such as methylene chloride in the presence of triethylamine or 4-dimethylaminopyridine. In addition, amine 25 by reaction with trimethylsilyl isocyanate (29; $R^{12b}$ is $(CH_3)_3Si$).

SCHEME 13

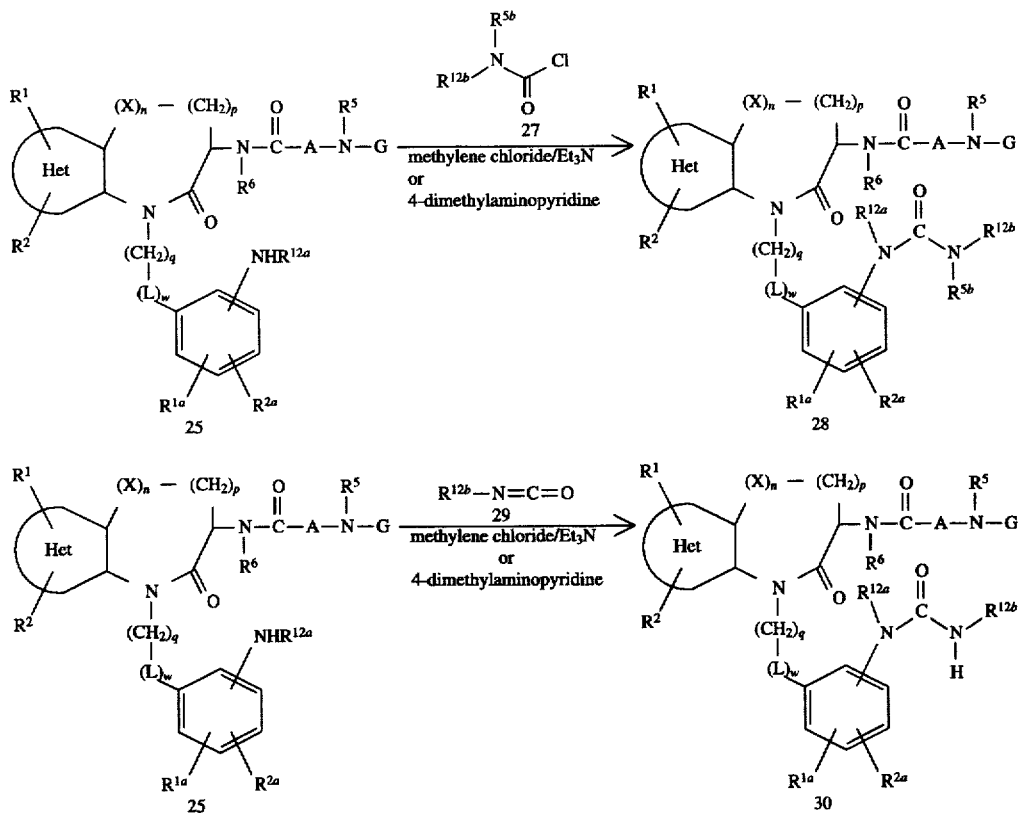

Alternatively, amine 24 is converted to an isocyanate 31 by treatment with phosgene or an equivalent reagent such as bis(trichloromethyl)carbonate (triphosgene) as indicated in Scheme 14. Subsequent reaction of 31 with primary or secondary amines in an inert solvent such as methylene chloride gives the corresponding urea derivative 28 in good yield. Isocyanate 31 is also converted to substituted semicarbazides 32 or hydroxy- or alkoxyureas 33 by reaction with substituted hydrazines or hydroxy- or alkoxylamines, respectively.

SCHEME 14

-continued
SCHEME 14

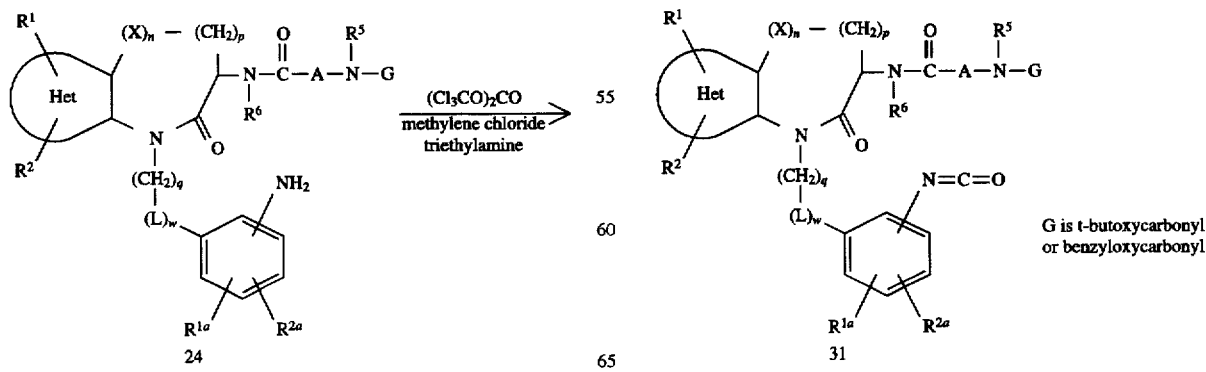

G is t-butoxycarbonyl or benzyloxycarbonyl

27
-continued
SCHEME 14

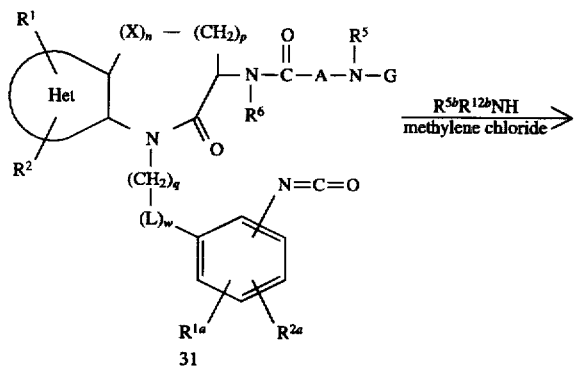
31

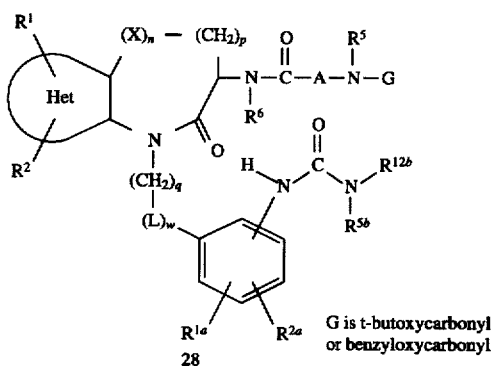
G is t-butoxycarbonyl or benzyloxycarbonyl
28

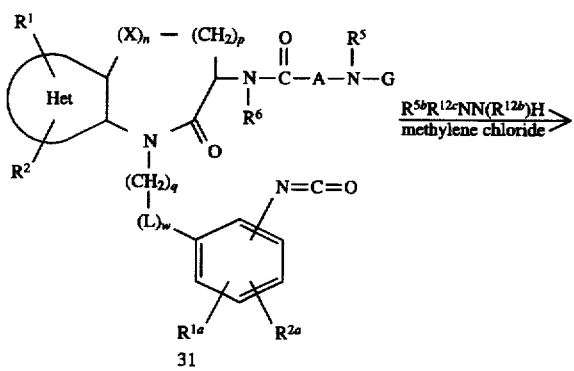
31

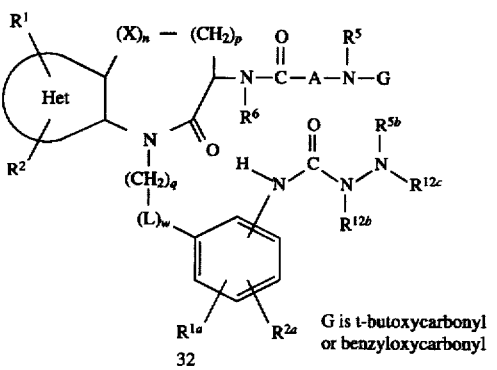
G is t-butoxycarbonyl or benzyloxycarbonyl
32

28
-continued
SCHEME 14

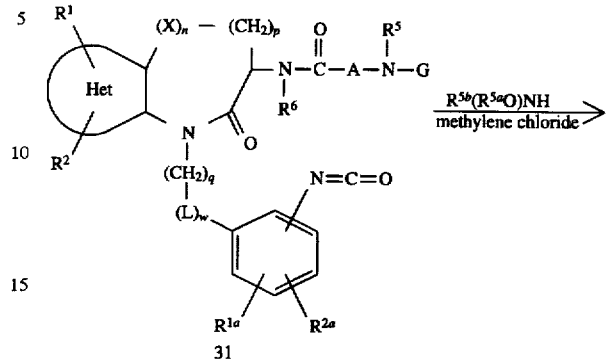
31

G is t-butoxycarbonyl or benzyloxycarbonyl
33

Intermediates of formula II where $R^{3a}$ or $R^{3b}$ is a carbazate or carbamate derivative where attachment to the phenyl ring is through the oxygen atom of the carbazate or carbamate linkage are prepared from acetophenone intermediate 34 as indicated in Scheme 15.

SCHEME 15

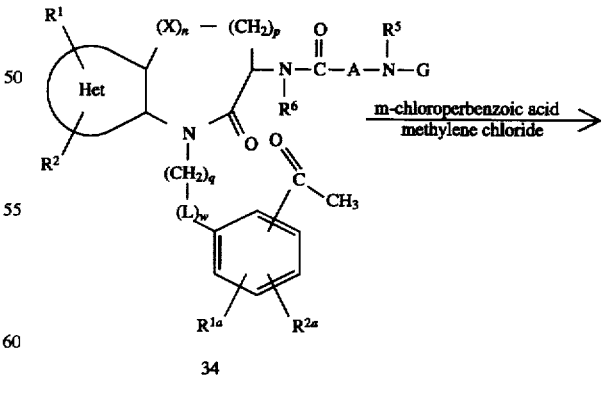
34

-continued
SCHEME 15

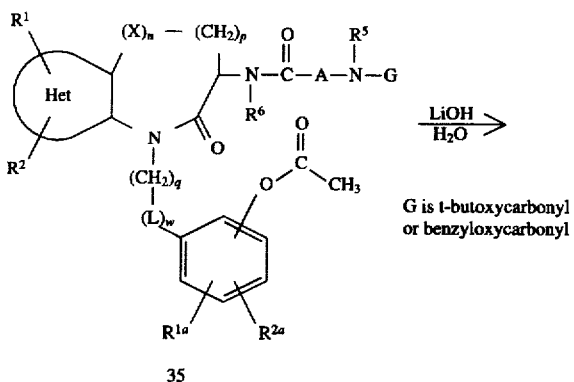

35

G is t-butoxycarbonyl
or benzyloxycarbonyl

LiOH / H₂O →

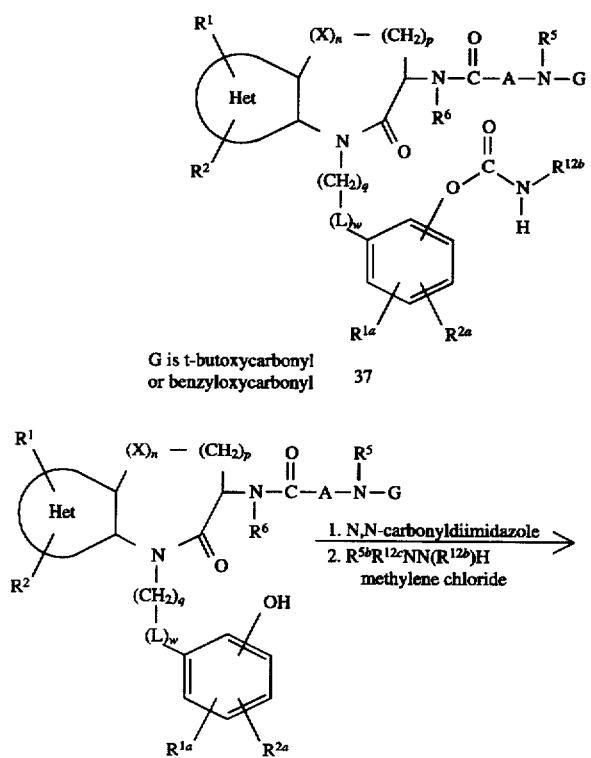

36

$R^{12b}-N=C=O$
29
CH₂Cl₂/Et₃N
or
DMAP
→

[structure]

37

G is t-butoxycarbonyl
or benzyloxycarbonyl

[structure]

36

1. N,N-carbonyldiimidazole
2. $R^{5b}R^{12c}NN(R^{12b})H$
methylene chloride
→

-continued
SCHEME 15

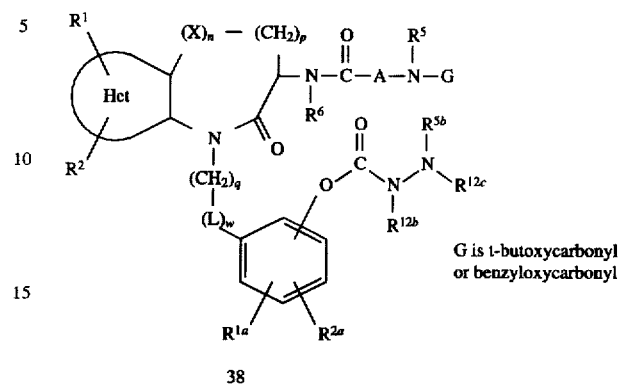

38

G is t-butoxycarbonyl
or benzyloxycarbonyl

Oxidative rearrangement of 34 through the use of a peroxy-carboxylic acid (Baeyer-Villager reaction) such as m-chloroperbenzoic acid gives the ester 35 which is hydrolyzed in the presence of a strong base such as sodium or lithium hydroxide to give phenol 36. Reaction of 36 with isocyanate 29 leads directly to carbamate 37. Additionally, treatment of 36 with N,N'-carbonyldiimidazole in dimethylformamide can form an activated intermediate which will react with substituted hydrazine reagents to give a carbazate product 38.

Intermediates of formula II wherein $R^{3a}$ or $R^{3b}$ is $R^{5b}R^{12b}NCON(R^{12a})CH_2—$, $R^{5b}R^{12b}NCSN(R^{12a})CH_2—$, $R^{5b}R^{12c}NN(R^{12b})CSN(R^{12a})CH_2—$, $R^{5b}R^{12c}NN(R^{12b})—CON(R^{12a})CH_2—$ or $R^{13}OCON(R^{12a})CH_2—$ can be prepared from the t-butyl ester intermediate 39 as described in Scheme 16. Removal of the t-butyl ester through the use of trifluoroacetic acid will give the carboxylic acid 40. It may be appreciated by one skilled in the art that the protecting group G in 39 must therefore be compatible with the strongly acidic conditions employed for ester cleavage; hence G is taken as benzyloxycarbonyl. Conversion of the carboxylic acid to the benzylamine derivative 41 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 41 can be further elaborated to 42 by the aforementioned reductive amination procedure.

SCHEME 16
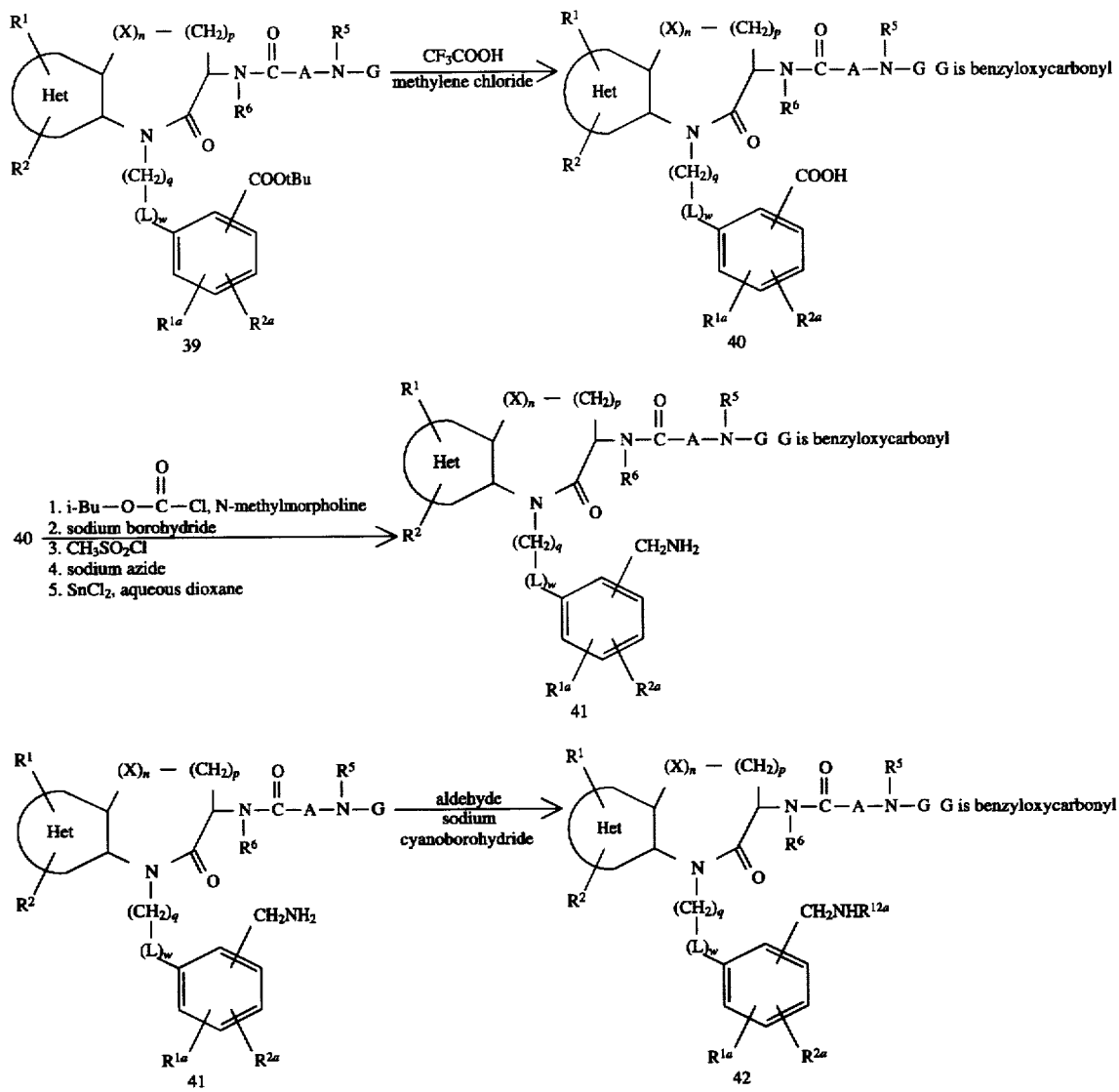
Reactions of amine 42 with the appropriate reagents to form urea-linked compounds 43 and 44 and carbamate-linked compound 45 are illustrated in Scheme 17. Terminally unsubstituted urea 43, wherein $R^{12b}$ is hydrogen, is also prepared from amine 42 by reaction with trimethylsilyl isocyanate (29, $R^{12b}$ is $(CH_3)_3Si$).

SCHEME 17
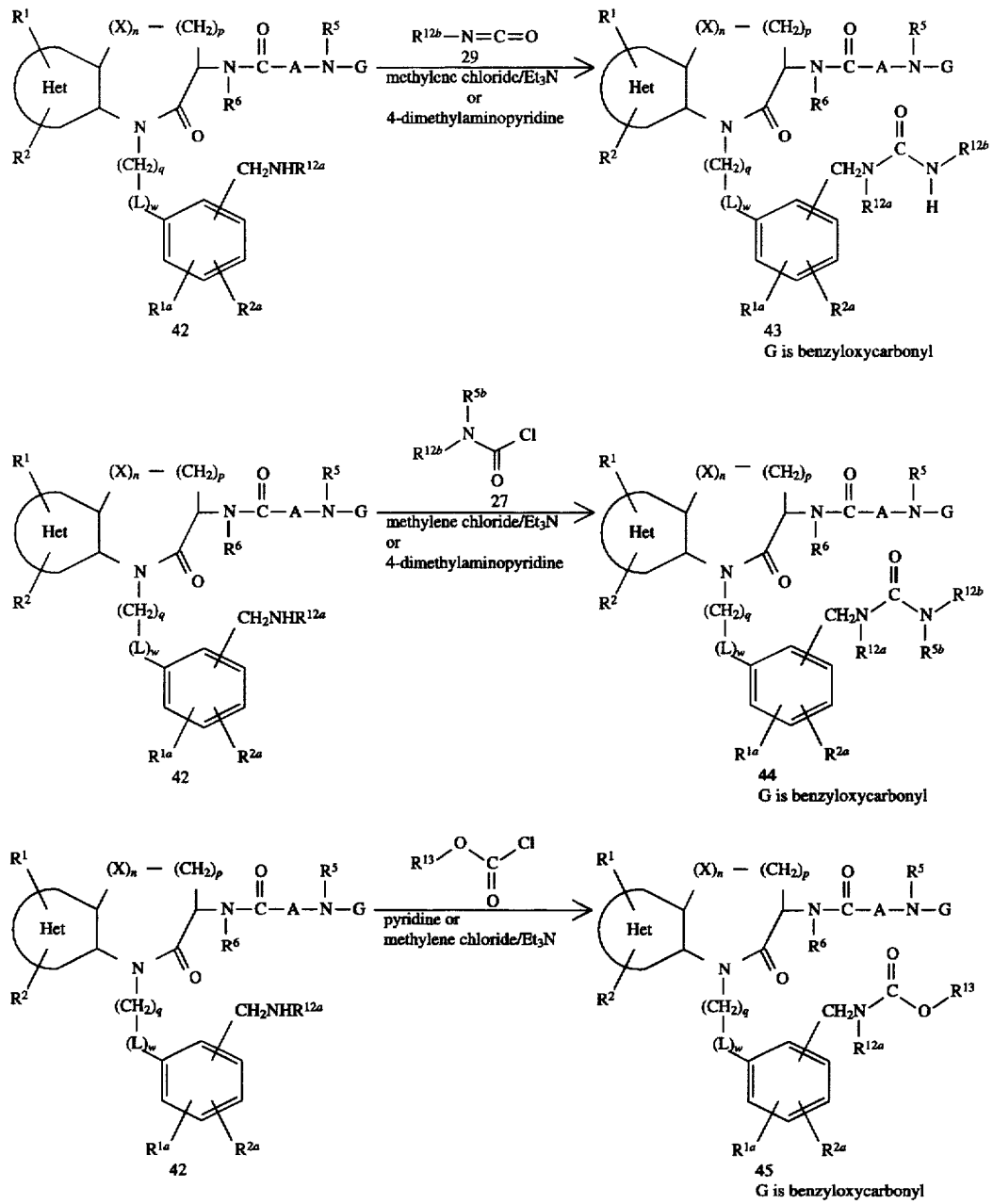
As shown in Scheme 18, hydrazide compound 46 can be prepared from intermediate 42 by a two-step procedure consisting of activation of the amine via treatment with N,N'-carbonyldiimidazole followed by treatment with the appropriately substituted hydrazine derivative $R^{5b}R^{12c}NN(R^{12b})H$.

SCHEME 18

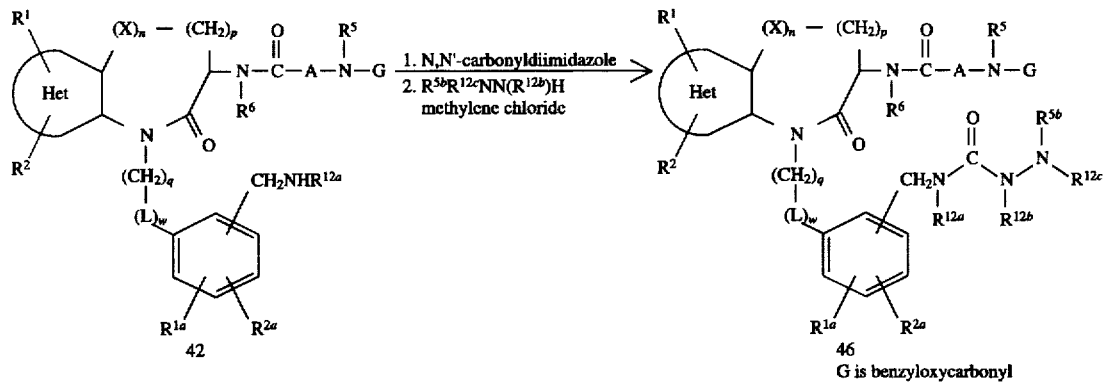

46
G is benzyloxycarbonyl

A useful preparation of the protected benzylamine intermediate 51 is shown in Scheme 19. Metallation of 4-bromobenzyl t-butyldiphenylsilylether 47 with n-butyllithium followed by treatment with triisopropyl borate gives the aryl boronic acid 48. Reaction of 48 with 2-bromo-N-(t-butoxycarbonyl)benzylamine 49 in the presence of tetrakis(triphenylphosphine)palladium(O) and sodium hydroxide in a mixed solvent system at elevated temperature gives the coupled product 50 in good yield. Desilylation and conversion to the O-methanesulfonate 51 is achieved by treatment with tetrabutylammonium fluoride followed by methanesulfonyl chloride. Reaction of 51 with intermediates of formula V is carried out using the conditions described in Scheme 6.

SCHEME 19

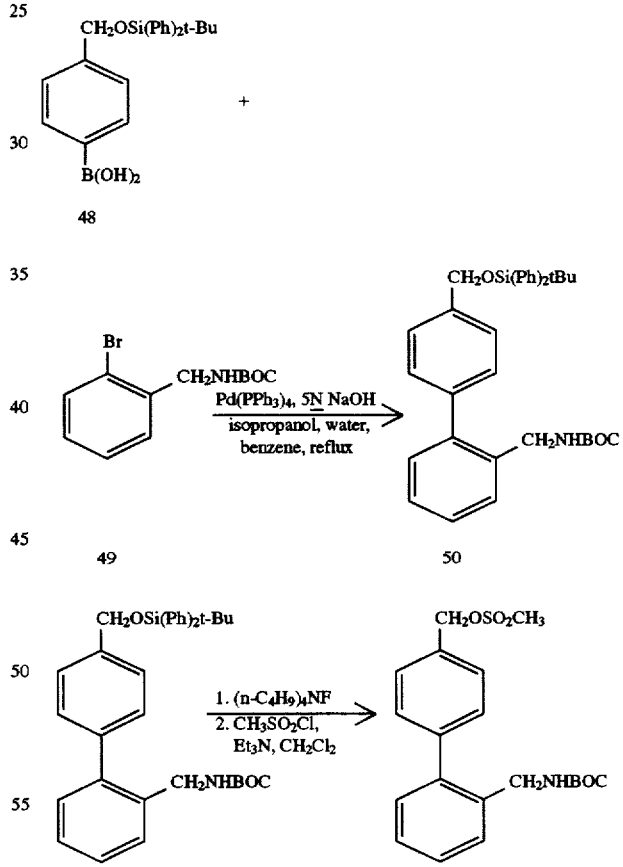

Compounds of formula I wherein $R^{3a}$ or $R^{3b}$ is taken as $R^{5b}R^{12b}$NCO are prepared by several methods. For example, as shown in Scheme 20, compound 52 wherein $R^{5b}$ and $R^{12b}$ are both hydrogen is conveniently prepared by hydrolysis of the nitrile precursor 12.

SCHEME 20

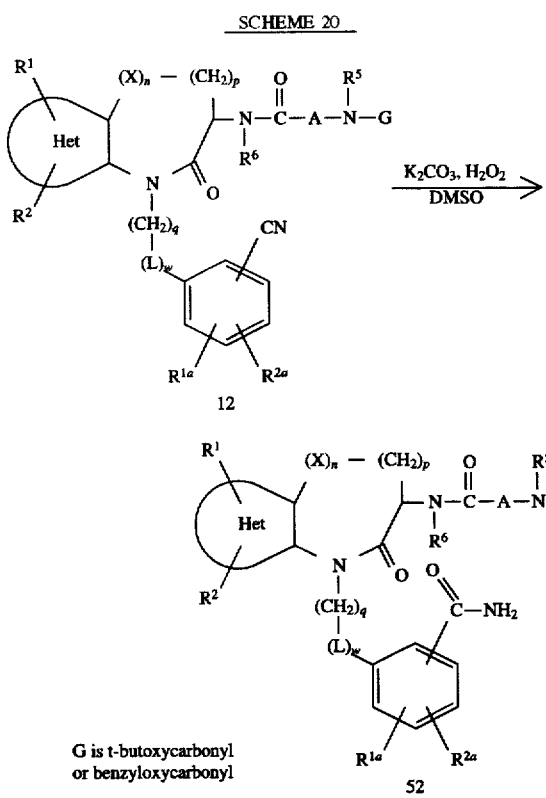

Thus, treatment of nitrile 12 with hydrogen peroxide and a strong base, such as potassium carbonate, in a polar solvent, such as dimethylsulfoxide at temperatures of 25° C. to 150° C. results in formation of the amide derivative 52. The precursor 12 is prepared from an appropriate alkylating agent VI, where $R^{3a}$ is cyano, as described in Scheme 6.

A useful method of preparing the alkylating agent 55 is outlined in Scheme 21

SCHEME 21

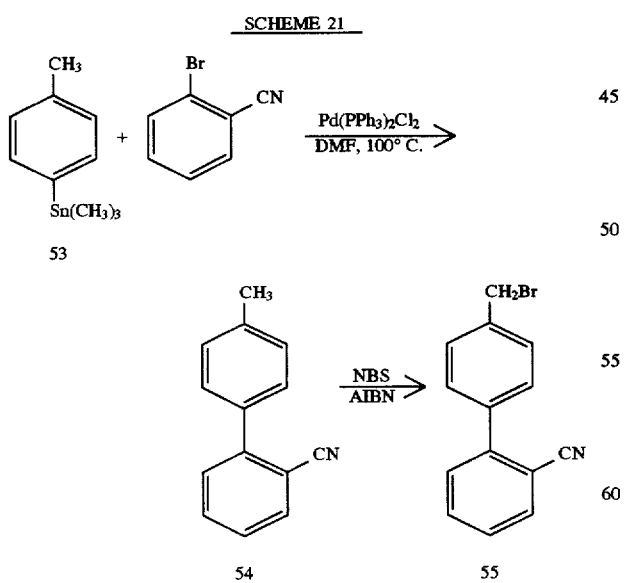

Thus, treatment of 4-(methylphenyl)trimethyl stannane 53 with 2-bromobenzonitrile in dimethylformamide at 100° C. in the presence of bis(triphenylphosphine)palladium(II) chloride results in coupling to form the biphenyl nitrile 54 in high yield. Conversion to bromide 55 is achieved by the aforementioned treatment with N-bromosuccinimide.

Compounds of formula I wherein $R^{3a}$ or $R^{3b}$ is taken as $R^{5b}R^{12b}NCO$— and $R^{5b}$ and/or $R^{12b}$ is other than hydrogen (56) are prepared from the corresponding carboxylic acid derivative 40 as shown in Scheme 22.

SCHEME 22

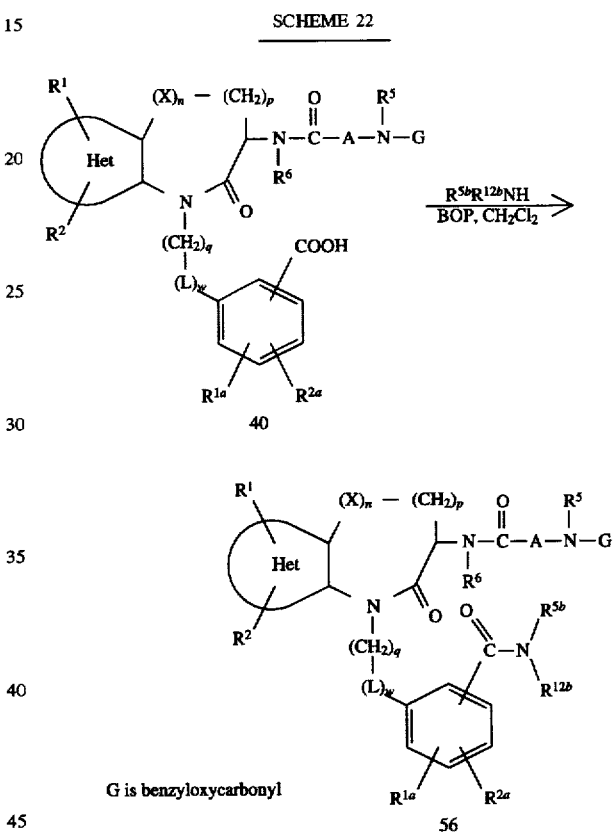

Coupling of the carboxylic acid derivative 40 with $R^{5b}R^{12b}NH$ is conveniently carried out by the use of the previously described coupling reagents benzotriazol-1-yloxytris(dimethylamino)phosphoiium hexafluorophosphate ("BOP") or benzotriazol-1-yloxytripyrrolidinophosphonium hexafluorophosphate ("PyBOP") in methylene chloride. The requisite carboxylic acid precursors are prepared as illustrated in Scheme 23 for the biphenyl compound 40.

SCHEME 23

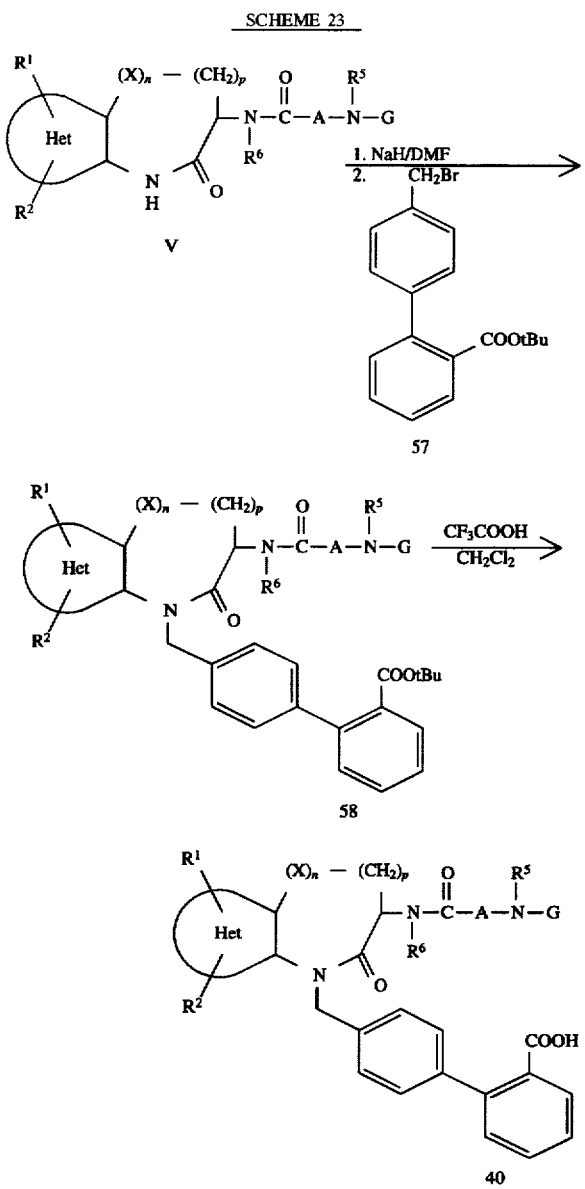

G is benzyloxycarbonyl

Alkylation of V with t-butyl 4'-bromomethyl-biphenyl-2-carboxylate 57 (prepared as described in EPO Publication 324,377) in the presence of sodium hydride as previously described in Scheme 6 gives the adduct 58 in high yield. Hydrolysis of the t-butyl ester to give the acid 40 is achieved by treatment with a strong acid, such as trifluoroacetic acid, in an inert solvent such as methylene chloride. It is noted that the protecting group G in this instance must be inert to strongly acidic conditions, for example G is benzyloxycarbonyl (CBz).

Conversion to intermediates of formula II is carried out by simultaneous or sequential removal of all protecting groups from intermediate VII as illustrated in Scheme 24.

SCHEME 24

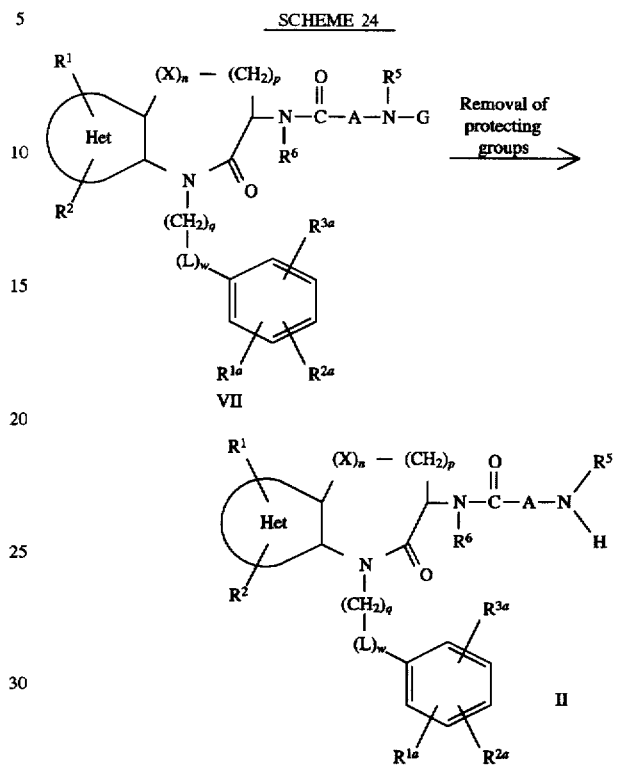

Removal of benzyloxycarbonyl (CBz) groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley and Sons, NY. 1981.

As shown in Scheme 25, intermediates of formula II are elaborated to compounds of formula I by reductive alkylation with an aldehyde by the aforementioned procedures. The products, obtained as hydrochloride or trifluoroacetate salts, are conveniently purified by reverse phase high performance liquid chromatography (HPLC) or by recrystallization.

SCHEME 25

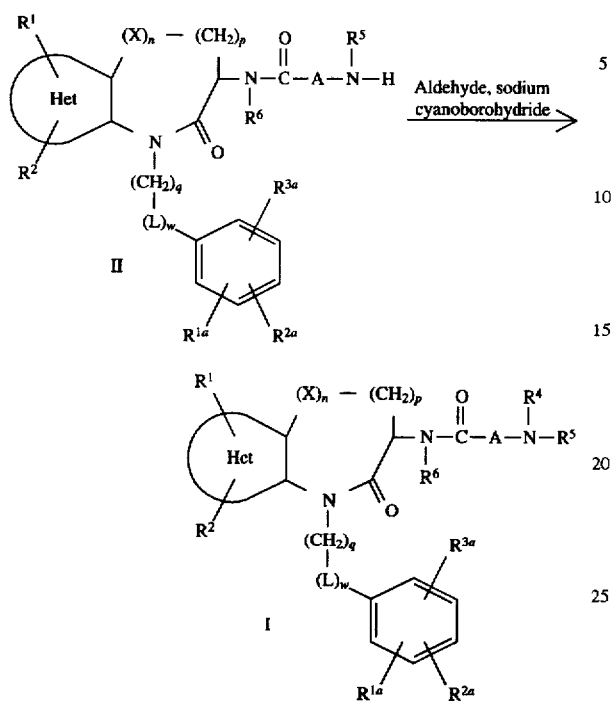

A route to the sub-class of compounds of formula I that can be described by formula IX is shown in Scheme 26.

SCHEME 26

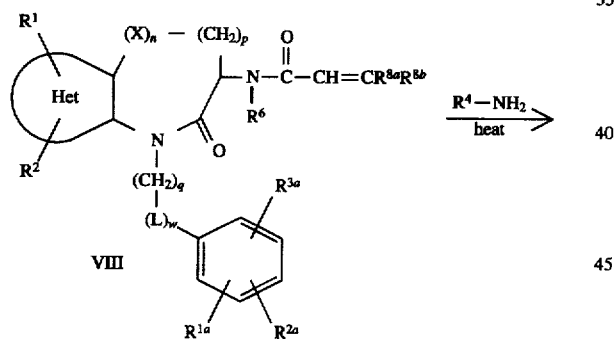

-continued
SCHEME 26

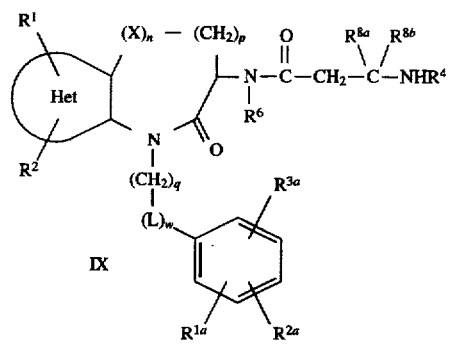

Thus, intermediates of formula VIII are reacted with $R^4$—$NH_2$ neat or in a polar solvent such as dimethylsulfoxide at temperatures of 50° C. to 200° C., to give compounds of formula IX. Intermediates of formula VIII may themselves be prepared by the transformations described in the preceding reaction schemes.

It should be appreciated by one skilled in the art that the order of the alkylation step (Scheme 6) and the reductive alkylation step (Scheme 25) may be reversed to facilitate the reaction or to avoid unwanted reaction products. Thus, as demonstrated in Scheme 27, intermediate V is deprotected using the aforementioned conditions, and the resulting amine intermediate X is reacted with an appropriate aldehyde under the reductive alkylation conditions described previously. The new intermediate thus obtained (XI), may then be treated with alkylating agent VI following the procedures described in Scheme 6 to give, after removal of any protecting groups, compounds of formula I.

SCHEME 27

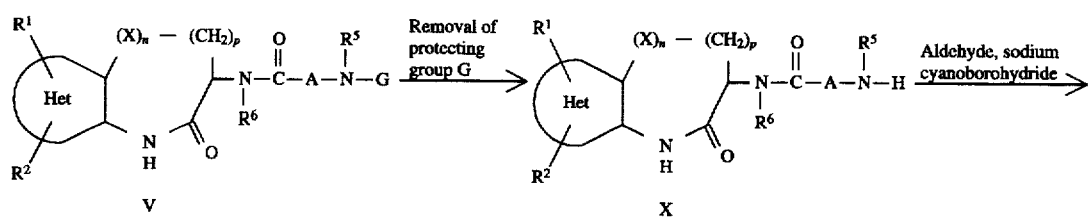

-continued
SCHEME 27

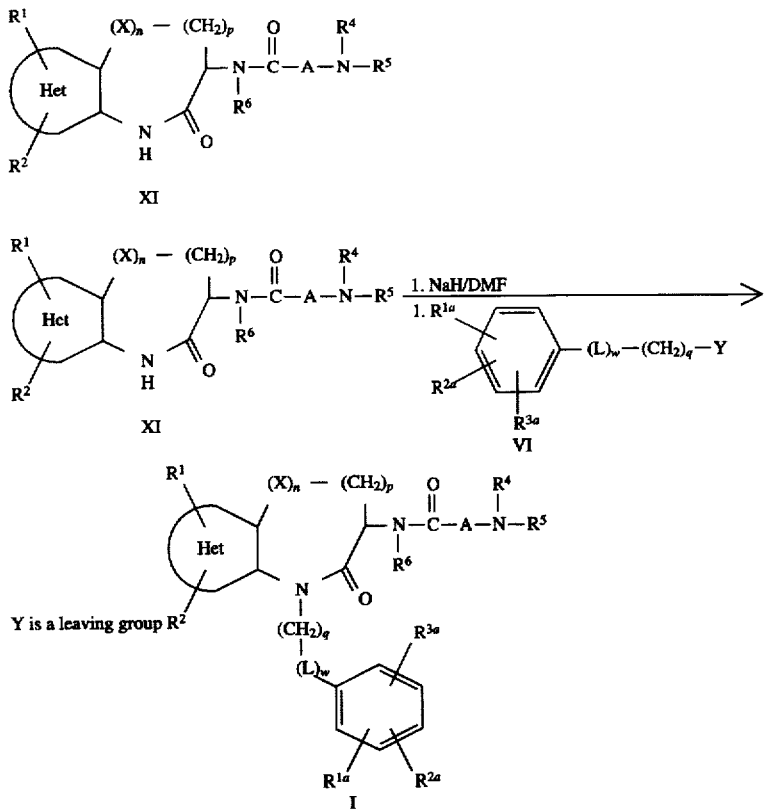

It is again noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A further use of the disclosed novel heterocyclic-fused lactam growth hormone secretagogues is in combination with other growth hormone secretagogues such as GHRP-6, GHRP-1 or GHRP-2 as described in U.S. Pat. No. 4,411, 890; and publications WO 89/07110 and WO 89/07111 and B-HT 920 or in combination with growth hormone releasing factor and its analogs or growth hormone and its analogs. A still farther use of the disclosed novel heterocyclic-fused lactam growth hormone secretagogues is in combination with α2 adrenergic agonists or $\beta_3$ adrenergic agonists in the treatment of obesity or in combination with parathyroid hormone or bisphosphonates, such as MK-217 (alendronate), in the treatment of osteoporosis. A still further use of the disclosed novel heterocyclic-fused lactam growth hormone secretagogues is in combination with IGF-1 to reverse the catabolic effects of nitrogen wasting as described by Kupfer, et al. *J. Clin. Invest.*, 91, 391 (1993).

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; prevention of catabolic side effects of glucocorticoids; treatment of osteoporosis; stimulation of the immune system; treatment of retardation; acceleration of wound healing; accelerating bone fracture repair; treatment of growth retardation, treating renal failure or insufficiency resulting in growth retardation; treatment of physiological short stature, including growth hormone deficient children; treating short stature associated with chronic illness; treatment of obesity and growth retardation associated with obesity; treating growth retardation associated with Prader-Willi syndrome and Turner's syndrome; accelerating the recovery and reducing hospitalization of burn patients; treatment of intrauterine growth retardation, skeletal dysplasia, hypercortisolism and Cushings syndrome; induction of pulsatile growth hormone release; replacement of growth hormone in stressed patients; treatment of osteochondrodysplasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; reducing cachexia and protein loss due to chronic illness such as cancer or AIDS. Treatment of hyperinsulinemia including nesidioblastosis; adjuvant treatment for ovulation induction; to stimulate thymic development and prevent the age-related decline of thymic function; treatment of immunosuppressed patients; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock and stimulation of wool growth in sheep.

The compounds of this invention can be administered by oral, parenteral (e.g., intramuscular, intraperitoneal, intravenous or subcutaneous injection or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/Kg of body weight daily are administered to patients and animals, e.g., mammals, to obtain effective release of growth hormone.

The following examples are provided for the purpose of further illustration only and are not intended to be limitations on the disclosed invention.

EXAMPLE 1

3-Amino-3-methyl-N-[6,7,8,9-tetrahydro-8-oxo-9-[[2'-(1H-tetrazol-5-yl)[1,1'-biphenyl]-4-yl]methyl]-5H-pyrido[2,3-b]azepin-7(R)-yl]-butanamide Step A: 8-Acetoxy-5,6,7,8-tetrahydroquinoline To 9.7 g of 5,6,7,8-tetrahydro quinoline in 36 mL of acetic acid was added 7.2 mL of 30% hydrogen peroxide and the mixture was warmed to 70° C. for 5 h. Another 7.2 mL of hydrogen peroxide was added and the mixture was stirred an additional 12.5 h at 70° C. The solution was then concentrated in vacuo. Solid potassium carbonate (20 g) was then added followed by 20 mL of chloroform and the thick paste was stirred at 20° C. for 4 h. The paste was then extracted 4× with 50 mL portions of boiling chloroform by filtration. The combined filtrate was concentrated in vacuo to yield 18 g of yellow oil. Acetic anhydride (50 mL) was then added to this oil and the mixture was heated at 90° C. under argon for 5 h. The excess acetic anhydride was then distilled off in vacuo and the residual liquid was distilled via Kugelrohr at 0.5 torr and 150° C. to afford 12.3 g of product characterized by its NMR.

Step B: 8-Hydroxy-5,6,7,8-tetrahydroquinoline

To 10 g of 8-acetoxy-5,6,7,8-tetrahydroquinoline in 30 mL of methanol was added 30 mL of 30% sodium hydroxide in water. The mixture was heated to reflux for 2 min and the methanol was removed in vacuo. The residual organic product was extracted with chloroform. The chloroform extracts were dried over sodium sulfate and evaporation of the solvent gave 8 g of product as an oil, characterized by its NMR.

Step C: 8-Oxo-5,6,7,8-tetrahydroquinoline

To a solution of 7 g of 8-hydroxy-5,6,7,8-tetrahydroquinoline in 150 mL of isopropyl acetate was added 14 mL of dimethyl sulfoxide and 33 mL of triethylamine. This mixture was stirred at −10° C. and 14 mL of phenyldichlorophosphate was added dropwise over 9 min. After an additional 15 min at 0° C. and 15 min at 20° C., the mixture was quenched with 50 mL of a saturated aqueous sodium bicarbonate solution. The product was extracted with ethyl acetate and flash chromatographic purification on silica gel afforded 2.22 g of ketone characterized by its NMR.

Step D: 8-Oximino-5,6,7,8-tetrahydroquinoline

A solution of 2.22 g of 8-oxo-5,6,7,8-tetrahydroquinoline, 2.1 g of hydroxylamine hydrochloride, and 4.1 g of sodium acetate in 15 mL of 3:1 ethanol-water was heated at 70° C. for 1 h. The reaction mixture was then diluted with water and extracted with dichloromethane. Evaporation of the extracts gave 1.95 g of product which was pure enough by NMR to be used in the next step.

Step E: 5,6,7,8-Tetrahydroquinoline-8-tosyloxime

To 1.95 g of 8-oximino-5,6,7,8-tetrahydroquinoline in 15 mL of pyridine was added 2.9 g of tosyl chloride. After 2 h the pyridine was removed in vacuo and the residual solid was taken up in 50 mL of chloroform and flash chromatographed on silica gel using ethyl acetate as eluent. 3.3 g of purified product was obtained characterized by its NMR and mass spectra.

Step F: 5,6,7,9-Tetrahydro-8H-pyrido[2,3-b]azepin-8-one

To 3.3 g of tosyl oxime (Step E) and 20 g of potassium acetate was added 70 mL of ethanol and 80 mL of water. The mixture was heated at 100° C. for 12 h, cooled to room temperature and diluted with water. The pH was adjusted to 10 with 10% sodium hydroxide and the mixture was extracted with dichloromethane. The combined extracts were evaporated to yield 2.5 g of product and flash chromatographic purification gave 1.35 g of the product characterized by its NMR and mass spectra.

Step G: 5,6,7,9-Tetrahydro-7-iodo-8H-pyrido[2,3-b]azepin-8-one

To a solution of 300 mg of 5,6,7,9-tetrahydro-8H-pyrido[2,3-b]azepin-8-one in 3 mL of dichloromethane at 0° C. was added 0.84 mL of N,N,N',N'-tetramethylethylenediamine (TMEDA) and 0.78 mL of trimethylsilyl iodide. After 30 min, 720 mg of solid iodine was added in one portion. The reaction mixture was stirred at 0° C. an additional 40 min before dichloromethane and excess aqueous sodium sulfite was added to reduce the excess iodine. The mixture was extracted with dichloromethane and the extracts were evaporated to yield 550 mg of the crude product. Flash chromatographic separation on silica gel with ethyl acetate gave 333 mg of purified product characterized by its NMR and mass spectra.

Step H: 7-Azido-5,6,7,9-tetrahydro-8H-pyrido[2,3-b]azepin-8-one

To 333 mg of the intermediate obtained in Step G in 6 mL of dimethylformamide (DMF) was added 600 mg of sodium azide. The mixture was stirred at 20° C. 20 h before addition of water and extraction with dichloromethane. The extracts were combined and dried over sodium sulfate. Evaporation of the solvent gave 223 mg of the product characterized by its NMR and mass spectra.

Step I: 7-Amino-5,6,7,9-tetrahydro-8H-pyrido[2,3-b]azepin-8-one

To 230 mg of the intermediate obtained in Step H in 10 mL of tetrahydrofuran was added 280 mg of triphenylphosphine. The mixture was stirred at 20° C. 18 h before 7 drops of water was added. The solution was then heated at 65° C. for 1 h. The solvent was removed in vacuo and the residue was flash chromatographed on silica gel using 100:20:5:3 (v:v) chloroformn:methanol:acetic acid:water to afford 209 mg of pure amine characterized by its NMR and mass spectra.

Step J: 4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step H without purification. $^1$H NMR (200 MHz, CDCl$_3$): δ1.45 (s, 6H), 2.75 (d, 3Hz, 2H), 5.9 (br s, 1H).

Step K: N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one (Step J), 800 mL of methylene chloride, 150 mL of triethylamine (1.08 mol) and 10.9 g (0.089 mol) of 4-dimethylaminopyridine. To the stirred solution, at room temperature was added dropwise over 15 minutes a solution of 235 g (1.077 mol) of di-t-butyl-dicarbonate in 300 mL of methylene chloride. The reaction mixture was stirred at room temperature overnight, then diluted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an orange solid. The material was used directly in Step I without purification. $^1$H NMR (200 MHz, CDCl$_3$): $\delta$1.50 (s, 9H), 1.54 (s, 6H), 2.77 (s, 2H).

Step L: 3-t-Butoxycarbonylamino-3-methylbutanoic acid

A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0°–5° C. and treated dropwise with 890 mL of 1.0M aqueous lithium hydroxide over 30 minutes. The reaction mixture was stirred at 0°–5° C. for 2 hours, then diluted with 1 L of ether and 1 L of water. The layers were allowed to separate and the aqueous layer was reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to give 173 g of a yellow oil that solidified upon standing. The material was slurried with warm hexane, then filtered and dried under high vacuum to afford 168.5 g (0.775 mol, 87%) of product as a white solid. $^1$H NMR (200 MHz, CDCl$_3$): $\delta$1.39 (s, 6H), 1.44 (s, 9H), 2.72 (s, 2H). FAB-MS: calculated for C$_{10}$H$_{19}$NO$_4$ 217; found 218 (M+H,54%).

Step M: [1,1-Dimethyl-3-oxo-3-[[6,7,8,9-tetrahydro-8-oxo-5H-pyrido[2,3-b]azepin-7-yl]amino]propyl]carbamic acid, 1,1-dimethylethyl ester To 68 mg of 3-t-butoxycarbonylamino-3-methylbutanoic acid in 1 mL of DMF was added 60 mg of 1-(3-dimethylaminopropyl)-3-ethylcarbodiimide hydrochloride (EDC). The mixture was stirred at 20° C. for 2 h before 50 mg of 7-amino-5,6,7,9-tetrahydro-8H-pyrido[2,3-b]azepin-8-one was added and the reaction was stirred an additional 18 h. The DMF was removed in vacuo and the residue was purified by preparative silica gel layer chromatography to yield 52 mg of the product characterized by its NMR and mass spectra.

Step N: 3-Amino-3-methyl-N-[6,7,8,9-tetrahydro-8-oxo-9-[[2'-(1H-tetrazol-5-yl)[1,1'-biphenyl]-4-yl]methyl]-5H-pyrido[2,3-b]azepin-7(R)-yl]butanamide To 31 mg of the intermediate obtained in Step M in 2 mL of DMF was added 20 mg of 60% sodium hydride/oil dispersion. After 2 min, 60 mg of N-triphenylmethyl-5-[2-(4'-bromomethylbiphen-4-yl)]tetrazole was added. After an additional 5 min, ice and saturated aqueous ammonium chloride solution was added to stop the reaction. The products were extracted with ethyl acetate and purified by PTLC on silica gel to afford 41 mg of the alkylated product. This was treated with 1 mL of neat trifluoroacetic acid for 2 min, then 3 mL of methanol and 3 drops of concentrated hydrochloric acid for 30 min. The solvent was removed in vacuo and PLC of the residual material gave 28 mg of the title compound characterized by its NMR and mass spectra.

EXAMPLE 2

3-Amino-N-[5,6,7,8-tetrahydro-5-oxo-4-[[2'-(1H-tetrazol-5-yl)[1,1'-biphenyl]-4-yl]methyl]-4H-thieno[3,2-b]azepin-6(R)-yl]-3-methylbutanamide Step A: 4-Oximino-4,5,6,7-tetrahydrothianaphthene A solution of 10.9 g of sodium acetate, 9.33 g of hydroxylamine hydrochloride and 10.1 g of 4-keto-4,5,6,7-tetrahydrothianaphthene in 22 mL of water and 66 mL of ethanol was heated to 50° C. for 2 hr, poured into water, extracted with ethyl acetate, and the solvent removed in vacuo to give 11.63 g of a crude mixture of E and Z oximes. Flash chromatography yielded 11.13 g of E-oxime and 188 mg of Z-oxime which were characterized by NMR and Mass spectroscopy.

Step B: 4,6,7,8-Tetrahydro-4H-thieno[3,2-b]azepin-5-one

A solution of 2.28 g of the E-oxime (Step A) and 2.6 g of tosyl chloride in 40 mL of pyridine was left to stir for 14 hr. The excess pyridine was removed in vacuo leaving a brown residue which gave 3.86 g of a mixture of tosyl oxime and unreacted oxime after flash chromatography. A suspension of 3.36 g of the mixture and 22.5g of potassium acetate in 70 mL of ethanol and 130 mL of water was heated to reflux for 14 hr, poured over ice, extracted with ethyl acetate and the solvents removed in vacuo. Flash chromatography gave 750 mg of clean lactam which was characterized by NMR and Mass spectroscopy.

Step C: 4,6,7,8-Tetrahydro-6-iodo-4H-thieno[3,2-b]azepin-5-one

A solution of 1.0 g of the lactam (Step B), 1.85 mL of TMEDA and 1.75 mL of TMSI in 10 mL of methylene chloride was stirred for 30 min at 0° C. After the addition of 2.3 g of iodine, the reaction mixture was left to stir for 2 hr at 0° C., warmed to room temperature, quenched with sodium sulfite solution and extracted with ethyl acetate. The insoluble material was filtered and dried in vacuo to give 476 mg of clean alpha-iodo lactam which was characterized by NMR and Mass spectroscopy. The solvents were removed from the extracts in vacuo to give 630 mg of alpha-iodo lactam which was contaminated with some starting lactam and characterized by NMR and Mass spectroscopy.

Step D: 6-Azido-4,6,7,8-tetrahydro-4H-thieno[3,2-b]azepin-5-one

A solution of 476 mg of the alpha-iodo lactam (Step C) and 530 mg of sodium azide in 5 mL of dimethyl formamide was heated at 70° C. for 2 hr, quenched with water, extracted with ethyl acetate and the solvents removed in vacuo to give 355 mg of clean alpha-azido lactam which was characterized by NMR and Mass spectroscopy.

Step E: 6-Amino-4,6,7,8-tetrahydro-4H-thieno[3,2-b]azepin-5-one

A solution of 370 mg of the alpha-azido lactam (Step D) and 470 mg of triphenylphosphine in 8 mL of distilled tetrahydrofuran was stirred for 40 hr at which point a precipitate formed. After adding 1 mL of water, the reaction mixture was heated to 70° C. for 2 hr, quenched with 10% sodium hydroxide solution, extracted with ethyl acetate and the solvents removed in vacuo. Flash chromatography, using dilute acetic acid in the eluent, gave 556 mg of the acetic acid salt of the alpha-amino lactam which was characterized by NMR and Mass Spectroscopy.

Step F: [1,1-Dimethyl-3-oxo-3-[(5,6,7,8-tetrahydro-5-oxo-4H-thieno[3,2-b]azepin-6-yl)amino]propyl]carbamic acid, 1,1-dimethylethyl ester A solution of 190 mg of the acetic acid salt of the alpha-amine lactam from Step E, 300 mg of 3-t-butoxycarbonylamino-3-methylbutanoic acid and 500 mg of bis(2-oxo-3-oxazolidinyl)phosphinic chloride in 5 mL of methylene chloride and 300 µl distilled trimethylamine was stirred for 18 hr, quenched with water, extracted with ethyl acetate and the solvents removed in vacuo. Flash chromatography gave 142 mg of [1,1-dimethyl-3-oxo-3-[(5,6,7,8-tetrahydro-5-oxo-4H-thieno[3,2-b]azepin-6-yl)amino]propyl]carbamic acid 1,1-dimethylethyl ester which was characterized by NMR and Mass spectroscopy.

51

Step G: 3-Amino-N-[5,6,7,8-tetrahydro-5-oxo-4-[[2'-(1H-tetrazol-5-yl)][1,1'-biphenyl]-4-yl]methyl]-4H-thieno[3,2-b]azepin-6(R)-yl]-3-methylbutanamide To a solution of 22 mg (0.058 mmol) of [1,1-dimethyl-3-oxo-3-[(5,6,7,8-tetrahydro-5-oxo-4H-thieno[3,2-b]azepin-6-yl)amino]propyl]carbamic acid 1,1-dimethylethyl ester (Step F) in 1 mL of DMF was added 20 mg of sodium hydride (60% oil dispersion). After 5 min at 20°°C., 34 mg of N-triphenylmethyl-5-[2-(4'-bromomethylbiphen-4-yl)] tetrazole was added. After another 15 min, the reaction was quenched with water and extracted with ethyl acetate. The extracts were combined, dried (sodium sulfate), filtered, and evaporated to yield 67 mg of crude products. Preparative layer chromatographic (PLC) purification on silica gel gave 25 mg of protected product. This was dissolved in 0.25 mL of neat trifluoroacetic acid for 2 min then 1 mL of methanol and 2 drops of conc. HCl was added. The mixture was stirred 2 h at 20° C. The solvent and acids were removed in vacuo, and PLC of the crude gave 10 mg of the title compound characterized by its mass and NMR spectra.

EXAMPLE 3

N-[1,4,5,6,7,8-hexahydro-5-oxo-4-[[2'-($H_1$-tetrazol-5-yl)[1,1'-biphenyl]-4-yl]methyl]pyrrolo[3,2-b]azepin-6(R)-yl]-3-amino-3-methylbutanamide Step A: 4-Oximino-4,5,6,7-tetrahydroindole A solution of 6.08 g of sodium acetate, 5.15 g of hydroxylamine hydrochloride, and 5.25 g of 4-keto-4,5,6,7-tetrahydro indole in 12 mL of water and 36 mL of ethanol was heated at 50° C. for 3 hr, quenched in water, extracted with ethyl acetate and dried over magnesium sulfate. The solvents were removed in vacuo to give a mixture of oxime isomers which was characterized by NMR and Mass spectroscopy.

Step B: E-4-(O-4-methylphenylsulfonyl)oximino-4,5,6,7-tetrahydroindole

A solution of 600 mg of the oxime mixture from Step A and 770 mg of tosyl chloride in 13 mL of pyridine was stirred at room temperature for 20 hr and then the solvents removed in vacuo. Flash chromatography yielded 267 mg of the E-tosyloxime which was characterized by NMR and Mass spectroscopy.

Step C: 4,6,7,8-Tetrahydro-pyrrolo[3,2-b]azepin-5(1H)-one

A solution of 2.3 g of the E-tosyloxime (Step B) and 22 g of potassium acetate in 80 mL of ethanol and 160 mL of water was heated to reflux for 3 hr, poured into ice water, extracted with ethyl acetate and chloroform, dried over sodium sulfate, and the solvents removed in vacuo. Flash chromatography yielded 1.06 g of lactam which was characterized by NMR and Mass spectroscopy.

Step D: 4,6,7,8-Tetrahydro-6-iodo-pyrrolo[3,2-b]azepin-5 (1H)-one

To a solution of 1.06 g of the lactam obtained in Step C in 10 mL of methylene chloride and 3.2 mL of TMEDA cooled to 0° C. was added 4.0 mL of trimethylsilyl iodide and stirred for 15 min. After the addition of 2.7 g of iodide, the reaction mixture was stirred for 20 hr while warming to room temperature, quenched with sodium sulfite solution, extracted with ethyl acetate and chloroform, dried over sodium sulfate, and the solvents removed in vacuo to give 1.93 g of material.

Step E: 6-Azido-4,6,7,8-tetrahydro-pyrrolo[3,2-b]azepin-5(1 H)-one

A solution of 1.93 g of the alpha-iodo lactam crude material (Step D) and 2.3 g of sodium azide in 20 mL of dimethyl formamide was heated to 60° C. for 3 hr, quenched with water, extracted with ethyl acetate and chloroform, dried over sodium sulfate, and the solvents removed in vacuo. Flash chromatography gave 426 mg of alpha-azido lactam which was characterized by NMR and Mass spectroscopy.

Step F: 6-Amino-4,6,7,8-tetrahydro-pyrrolo[3,2-b]azepin-5 (1H)-one

A solution of 426 mg of alpha-azido lactam (Step E) and 586 mg of triphenylphosphine in 15 mL of TBF was stirred at room temperature for 40 hr at which point a precipitate formed. After the addition of 1 mL of water, the reaction mixture was heated at 60° C. for 3 hr, cooled down, and the solvents removed in vacuo. Flash chromatrography using dilute acetic acid in the eluent gave 444 mg of the acetic acid salt of the alpha-amino lactam which was characterized by NMR and Mass spectroscopy.

Step G: [1,1-Dimethyl-3-oxo-3-[(5,6,7,8-tetrahydro-5-oxo-4H-pyrrolo[3,2-b]azepin-6-yl)amino]propyl]carbamic acid 1,1-dimethylethyl ester A solution of 100 mg of 3-t-butoxycarbonylamino-3-methylbutanoic acid in 5 mL of DME and 65 µl of N-methylmorpholine was cooled to −15° C. After the addition of 60 µl of isobutylchloroformate, the reaction mixture was left to stir for 3 hr at which point a precipitate formed. The precipitate was filtered off, washed with DME, and the mother liquors concentrated to give liquid product. A solution of the liquid product and 33 mg of the acetic acid salt of the alpha-amino lactam (Step F) in 2 mL of methylene chloride and 200 Al of triethylamine was stirred for 48 hr and the solvents removed in vacuo. Flash chromatography gave 30 mg of the alpha-amide lactam which was characterized by NMR and Mass spectroscopy.

Step H: N-[1,4,5,6,7,8-hexahydro-5-oxo-4-[[2'-(1H-tetrazol-5-yl)-[1,1'-biphenyl]-4-yl]methyl]pyrrolo[3,2-b]azepin-6(R)-yl]-3-amino-3-methylbutanamide To a solution of 30 mg of amide-lactam (Step G) in 1.5 mL of DMF was added 10 mg of sodium hydride (60% oil dispersion). After 5 min at 20° C., 47 mg of N-triphenylmethyl-5-[2-(4'-bromomethylbiphen4-yl)]-tetrazole was added. The mixture was stirred 15 min and water was added to quench the reaction. The mixture was extracted with ethyl acetate and purified by PLC and the protecting groups were removed as described in Example 2, Step G to afford 8 mg of product characterized by its NMR and mass spectra.

What is claimed is:

1. A compound of the formula:

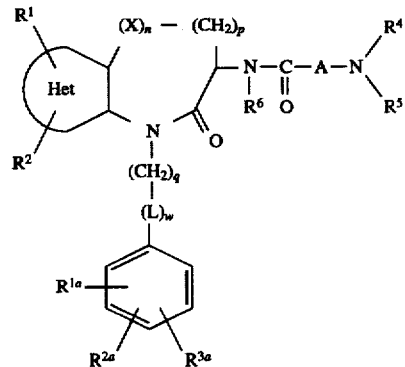

wherein:

L is

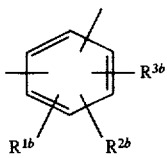

n is 0 or 1;
p is 0 to 3;
q is 0 to 4;
w is 0 or 1;
X is C=O, O, S(O)$_m$,

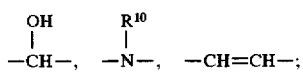

m is 0 to 2;

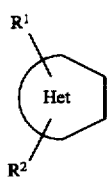

is thiophene which is independently disubstituted with $R^1$ and $R^2$;

$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, $C_1$–$C_3$ perfluoroalkoxy, —S(O)$_m$$R^{7a}$, cyano, nitro, $R^{7b}$O(CH$_2$)$_v$—, $R^{7b}$COO(CH$_2$)$_v$—, $R^{7b}$OCO(CH$_2$)$_v$—, $R^{5b}R^{12b}$N(CH$_2$)$_v$—, $R^{5b}R^{12b}$NCO(CH$_2$)$_v$—, phenyl or substituted phenyl where the substituents on the phenyl are 1 to 3 of halogen, $C_1$–$C_6$ alkyl, $C_1$–$C_6$ alkoxy, or hydroxy; v is 0 to 3 and m is 0 to 2;

$R^{7a}$ and $R^{7b}$ are independently hydrogen; $C_1$–$C_3$ perfluoroalkyl; $C_1$–$C_6$ alkyl; substituted $C_1$–$C_6$ alkyl where the substitutents are phenyl or substituted phenyl where the substitutents on the phenyl are 1 to 3 of halogen, $C_1$–$C_6$ alkyl, $C_1$–$C_6$ alkoxy or hydroxy; phenyl; or substituted phenyl where the substitutents on the phenyl are 1 to 3 of halogen, $C_1$–$C_6$ alkyl, $C_1$–$C_6$ alkoxy or hydroxy;

$R^{3a}$ and $R^{3b}$ are independently hydrogen, $R^9$, $C_1$–$C_6$ alkyl substituted with $R^9$, phenyl substituted with $R^9$ or phenoxy substituted with $R^9$;

$R^9$ is

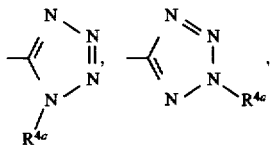

$R^{7b}$O(CH$_2$)$_v$—, $R^{7b}$COO(CH$_2$)$_v$—, $R^{7b}$OCO(CH$_2$)$_v$—, $R^{7b}$CO(CH$_2$)$_v$—, $R^{7b}$O(CH$_2$)$_v$CO—, $R^{5b}R^{12b}$N(CH$_2$)$_v$—,
$R^{5b}R^{12b}$NCO(CH$_2$)$_v$—, $R^{5b}R^{12b}$NCS (CH$_2$)$_v$—,
$R^{5b}R^{12c}$NN(R$^{12b}$)CO(CH$_2$)$_v$—,
$R^{5b}R^{12c}$NN(R$^{12b}$)CS(CH$_2$)$_v$—,
$R^{5b}R^{12b}$NCON(R$^{12a}$)(CH$_2$)$_v$—,
$R^{5b}R^{12b}$NCSN(R$^{12a}$)(CH$_2$)$_v$—,
$R^{5b}R^{12c}$NN(R$^{12b}$)CSN(R$^{12a}$)(CH$_2$)$_v$—,
$R^{5b}R^{12c}$NN(R$^{12b}$)CON(R$^{12a}$)(CH$_2$)$_v$—,
$R^{5b}R^{12c}$NN(R$^{12b}$)COO(CH$_2$)$_v$—, $R^{5b}R^{12b}$NCOO (CH$_2$)$_v$—
or $R^{13}$OCON(R$^{12}$a)(CH$_2$)$_v$—, where v is 0 to 3;

$R^{12a}$, $R^{12b}$ and $R^{12c}$ are independently $R^{5a}$, OR$^{5a}$ or COR$^{5a}$, $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$–$C_3$ perfluoroalkyl; $C_1$–$C_6$ alkyl; substituted $C_1$–$C_6$ alkyl, where the substitutents are hydroxy, —NR$^{10}R^{11}$, carboxy, phenyl or substituted phenyl where the substituents on the phenyl are 1 to 3 of halogen, $C_1$–$C_6$ alkyl, $C_1$–$C_6$ alkoxy or hydroxy; phenyl; or substituted phenyl where the substituents on the phenyl are 1 to 3 of halogen, $C_1$–$C_6$ alkyl, $C_1$–$C_6$ alkoxy or hydroxy;

$R^{10}$ and $R^{11}$ are independently hydrogen, $C_1$–$C_6$ alkyl, phenyl, phenyl $C_1$–$C_6$ alkyl, $C_1$–$C_5$ alkoxycarbonyl or $C_1$–$C_5$ alkanoyl-$C_1$–$C_6$ alkyl;

$R^4$, $R^{4a}$, $R^5$, $R^{5a}$ and $R^{5b}$ are independently hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl or substituted $C_3$–$C_{10}$ alkynyl where the substituents on the phenyl, alkyl, alkenyl or alkynyl are 1 to 5 of hydroxy, $C_1$–$C_6$ alkoxy, $C_3$–$C_7$ cycloalkyl, fluoro, phenyl independently disubstituted with $R^1$ and $R^2$, phenyl $C_1$–$C_3$ alkoxy independently disubstituted with $R^1$ and $R^2$, $C_1$–$C_{20}$-alkanoyloxy, $C_1$–$C_5$ alkoxycarbonyl, carboxy, formyl or —NR$^{10}R^{11}$ where $R^1$, $R^2$, $R^{10}$ and $R^{11}$ are as defined above; or $R^4$ and $R^5$ can be taken together to form —(CH$_2$)$_r$—B—(CH$_2$)$_s$— where B is CHR$^1$, O, S(O)$_m$ or N—R$^{10}$, r and s are independently 1 to 3, m is 0, 1 or 2 and $R^1$ and $R^{10}$ are as defined above;

$R^6$ is hydrogen, $C_1$–$C_{10}$ alkyl, phenyl or phenyl $C_1$–$C_{10}$ alkyl;

A is

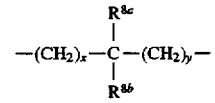

where x and y are independently 0–3;

$R^{8a}$ and $R^{8b}$ are independently hydrogen, $C_1$–$C_{10}$ alkyl, trifluoromethyl, phenyl independently disubstituted with $R^1$ and $R^2$, substituted $C_1$–$C_{10}$ alkyl where the substitutents are from 1 to 3 of imidazolyl, indolyl, hydroxy, fluoro, —S(O)$_m$$R^{7a}$, $C_1$–$C_6$ alkoxy, $C_3$–$C_7$ cycloalkyl, phenyl independently disubstituted with $R^1$ and $R^2$, phenyl $C_1$–$C_3$ alkoxy independently disubstituted with $R^1$ and $R^2$, $C_1$–$C_5$ alkanoyloxy, $C_1$–$C_5$ alkoxycarbonyl, carboxy, formyl or —NR$^{10}R^{11}$ where $R^1$, $R^2$, $R^{7a}$, $R^{10}$, $R^{11}$ and m are as defined above; or $R^{8a}$ and $R^{8b}$ can be taken together to form —(CH$_2$)$_t$— where t is 2 to 6; and $R^{8a}$ and $R^{8b}$ can independently be joined to one or both of $R^4$ and $R^5$ to form alkylene bridges between the terminal nitrogen and the alkyl portion of the A group wherein the bridge contains from one to five carbon atoms;

and pharmaceutically acceptable salts thereof.

2. The compound of claim 1 wherein:

n is 0 or 1;
p is 0 to 3;
q is 0 to 2;
w is 0 or 1;
X is O, S(O)$_m$,

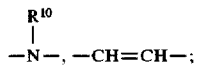
—N—, —CH=CH—;

m is 0 to 2;

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents on the phenyl are 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl where the substitutents are phenyl; phenyl and v is 0 to 3;

$R^{3a}$ and $R^{3b}$ are independently hydrogen, $R^9$, $C_1$-$C_6$ alkyl substituted with $R^9$, phenyl substituted with $R^9$ or phenoxy substituted with $R^9$;

$R^9$ is

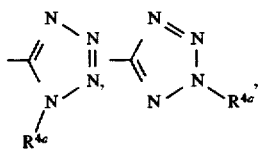

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^{5b}$R$^{12b}$N(CH$_2$)$_v$—, R$^{5b}$R$^{12b}$NCO(CH$_2$)$_v$—, R$^{5b}$R$^{12b}$NCS(CH$_2$)$_v$—, R$^{5b}$R$^{12c}$NN(R$^{12b}$)CO(CH$_2$)$_v$—, R$^{5b}$R$^{12b}$NCON(R$^{12a}$)(CH$_2$)$_v$—, R$^{5b}$R$^{12b}$NCSN(R$^{12a}$)(CH$_2$)$_v$—, R$^{5b}$R$^{12c}$NN(R$^{12b}$)CSN(R$^{12a}$)(CH$_2$)$_v$—, R$^{5b}$R$^{12c}$NN(R$^{12b}$)CON(R$^{12a}$)(CH$_2$)$_v$—, R$^{5b}$R$^{12c}$NN(R$^{12b}$)COO(CH$_2$)$_v$—, R$^{5b}$R$^{12b}$NCOO(CH$_2$)$_v$—
or R$^{13}$OCON(R$^{12a}$)(CH$_2$)$_v$—, and v is 0 to 3;

$R^{12a}$, $R^{12b}$ and $R^{12c}$ are independently $R^{5a}$, OR$^{5a}$ or COR$^{5a}$, $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$-$C_3$ perfluoroalkyl; $C_1$-$C_6$ alkyl; substituted $C_1$-$C_6$ alkyl, where the substitutents are hydroxy, —NR$^{10}$R$^{11}$, carboxy, phenyl or substituted phenyl where the substituents on the phenyl are 1 to 3 of halogen, $C_1$-$C_6$ alkyl, $C_1$-$C_6$ alkoxy or hydroxy; phenyl; or substituted phenyl where the substituents on the phenyl are 1 to 3 of halogen, $C_1$-$C_6$ alkyl, $C_1$-$C_6$ alkoxy or hydroxy;

$R^{10}$ and $R^{11}$ are independently hydrogen, $C_1$-$C_6$ alkyl, phenyl $C_1$-$C_6$ alkyl, or $C_1$-$C_5$ alkanoyl-$C_1$-$C_6$ alkyl;

$R^4$, $R^{4a}$, $R^5$, $R^{5a}$ and $R^{5b}$ are independently hydrogen, phenyl, substituted phenyl, $C_1$-$C_{10}$ alkyl, substituted $C_1$-$C_{10}$ alkyl where the substituents on the phenyl or the alkyl are 1 to 5 of hydroxy, C $1$-$C_6$ alkoxy, $C_3$-$C_7$ cycloalkyl, fluoro, phenyl independently disubstituted with $R^1$ and $R^2$, phenyl $C_1$-$C_3$ alkoxy independently disubstituted with $R^1$ and $R^2$, $C_1$-$C_{20}$-alkanoyloxy, $C_1$-$C_5$ alkoxycarbonyl, carboxy or formyl; $R^4$ and $R^5$ can be taken together to form —(CH$_2$)$_r$—B—(CH$_2$)$_s$— where B is CHR$^1$, O, S(O)$_m$ or N—R$^{10}$, r and s are independently 1 to 3, m is 0, 1 or 2 and $R^1$ and $R^{10}$ are as defined above;

$R^6$ is hydrogen, $C_1$-$C_{10}$ alkyl or phenyl $C_1$-$C_{10}$ alkyl;

A is

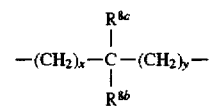

where x and y are independently 0–2;

$R^{8a}$ and $R^{8b}$ are independently hydrogen, $C_1$-$C_{10}$ alkyl, substituted $C_1$-$C_{10}$ alkyl where the substitutents are from 1 to 3 of imidazolyl, indolyl, hydroxy, fluoro, —S(O)$_m$R$^{7a}$, $C_1$-$C_6$ alkoxy, $C_3$-$C_7$ cycloalkyl, phenyl independently disubstituted with $R^1$ and $R^2$, phenyl $C_1$-$C_3$ alkoxy independently disubstituted with $R^1$ and $R^2$, $C_1$-$C_5$ alkanoyloxy, $C_1$-$C_5$ alkoxycarbonyl, carboxy, formyl or —NR$^{10}$R$^{11}$ where $R^1$, $R^2$, $R^{7a}$, $R^{10}$, $R^{11}$ and m are as defined above; or $R^{8a}$ and $R^{8b}$ can be taken together to form —(CH$_2$)$_t$— where t is 2 to 4; and $R^{8a}$ and $R^{8b}$ can independently be joined to $R^5$ to form alkylene bridges between the terminal nitrogen and the alkyl portion of the A group wherein the bridge contains from one to five carbon atoms;

and pharmaceutically acceptable salts thereof.

3. The compound of claim 2 wherein:

n is 0 or 1;
p is 0 to 2;
q is 0 to 2;
w is 0 or 1;
X is S(O)$_m$ or —CH=CH—;
m is 0 or 1;

$R^1$, $R^2$, $R^{1a}$, $R^{2a}$, $R^{1b}$ and $R^{2b}$ are independently hydrogen, halogen, $C_1$-$C_7$ alkyl, $C_1$-$C_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents on the phenyl are 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl or substituted $C_1$-$C_6$ alkyl where the substitutents are phenyl and v is 0 to 2;

$R^{3a}$ and $R^{3b}$ are independently hydrogen, $R^9$, $C_1$-$C_6$ alkyl substituted with $R^9$ or phenoxy substituted with $R^9$;

$R^9$ is

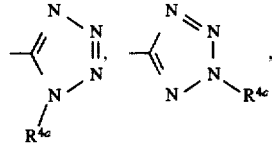

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^{5b}$R$^{12b}$N(CH$_2$)$_v$—, R$^{5b}$R$^{12b}$NCO(CH$_2$)$_v$—, R$^{5b}$R$^{12c}$NN(R$^{12b}$)CO(CH$_2$)$_v$—, R$^{5b}$R$^{12b}$NCON(R$^{12a}$)(CH$_2$)$_v$—, $R^{5b}R^{12c}NN(R^{12b})CSN(R^{12a})(CH_2)_v$—,
$R^{5b}R^{12c}NN(R^{12b})CON(R^{12a})(CH_2)_v$—,
$R^{5b}R^{12c}NN(R^{12b})COO(CH_2)_v$—, $R^{5b}R^{12b}NCOO(CH_2)_v$— or $R^{13}OCON(R^{12a})(CH_2)_v$—, where v is 0 to 2;

$R^{12a}$, $R^{12b}$ and $R^{12c}$ are independently $R^{5a}$ or $OR^5a$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;

$R^{13}$ is $C_1$–$C_6$ alkyl; substituted $C_1$–$C_6$ alkyl, where the substitutents are phenyl or substituted phenyl where the substituents on the phenyl are 1 to 3 of halogen, $C_1$–$C_6$ alkyl, $C_1$–$C_6$ alkoxy or hydroxy; phenyl; or substituted phenyl where the substituents on the phenyl are 1 to 3 of halogen, $C_1$–$C_6$ alkyl, $C_1$–$C_6$ alkoxy or hydroxy;

$R^{10}$ and $R^{11}$ are independently hydrogen, $C_1$–$C_6$ alkyl, phenyl $C_1$–$C_6$ alkyl, or $C_1$–$C_5$ alkanoyl-$C_1$–$C_6$ alkyl;

$R^4$, $R^{4a}$, $R^5$, $R^{5a}$ and $R^{5b}$ are independently hydrogen, $C_1$–$C_{10}$ alkyl or substituted $C_1$–$C_{10}$ alkyl where the substituents are from 1 to 5 of hydroxy, $C_1$–$C_6$ alkoxy, fluoro, phenyl independently disubstituted with $R^1$ and $R^2$, $C_1$–$C_{20}$-alkanoyloxy, $C_1$–$C_5$ alkoxycarbonyl or carboxy; where $R^1$ and $R^2$ are as defined above;

$R^6$ is hydrogen or $C_1$–$C_{10}$ alkyl;

A is

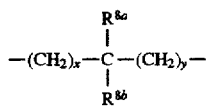

where x and y are independently 0–1;

$R^{8a}$ and $R^{8b}$ are independently hydrogen, $C_1$–$C_{10}$ alkyl, substituted $C_1$–$C_{10}$ alkyl where the substitutents are from 1 to 3 of imidazolyl, indolyl, hydroxy, fluoro, —$S(O)_mR^{7a}$, $C_1$–$C_6$ alkoxy, $C_3$–$C_7$ cycloalkyl, phenyl independently disubstituted with $R^1$ and $R^2$, phenyl $C_1$–$C_3$ alkoxy independently disubstituted with $R^1$ and $R^2$, $C_1$–$C_5$ alkanoyloxy, $C_1$–$C_5$ alkoxycarbonyl, carboxy, formyl or —$NR^{10}R^{11}$ where $R^1$, $R^2$, $R^{7a}$, $R^{10}$, $R^{11}$ and m are as defined above; or $R^{8a}$ and $R^{8b}$ can be taken together to form —$(CH_2)_t$— where t is 2; and $R^{8a}$ and $R^{8b}$ can independently be joined to $R^5$ to form alkylene bridges between the terminal nitrogen and the alkyl portion of the A group wherein the bridge contains from one to five carbon atoms;

and pharmaceutically acceptable salts thereof.

4. The compound of claim 3 wherein:

n is 0 or 1;
p is 0 to 2;
q is 1;
w is 1;
X is $S(O)_m$ or —CH=CH—;
m is 0 or 1;
$R^1$, $R^2$, $R^{1a}$, $R^{2a}$, $R^{1b}$ and $R^{2b}$ are independently hydrogen, halogen, $C_1$–$C_7$ alkyl, $C_1$–$C_3$ perfluoroalkyl, —$S(O)_mR^{7a}$, $R^{7b}O(CH_2)_v$—, $R^{7b}COO(CH_2)_v$—, phenyl or substituted phenyl where the substituents on the phenyl are 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_6$ alkyl or substituted $C_1$–$C_6$ alkyl where the substituents are phenyl and v is 0 or 1;

$R^{3a}$ and $R^{3b}$ are independently hydrogen, $R^9$ or $C_1$–$C_6$ alkyl substituted with $R^9$;

$R^9$ is

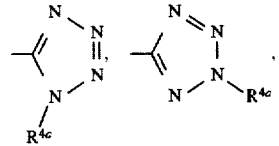

$R^{7b}O(CH_2)_v$—, $R^{7b}COO(CH_2)_v$—, $R^{7b}OCO(CH_2)_v$—, $R^{7b}CO(CH_2)_v$—, $R^{5b}R^{12b}N(CH_2)_v$—,
$R^{5b}R^{12b}NCO(CH_2)_v$—, $R^{5b}R^{12c}NN(R^{12b})CO(CH_2)_v$—,
$R^{5b}R^{12b}NCON(R^{12a})(CH_2)_v$—,
$R^{5b}R^{12c}NN(R^{12b})CON(R^{12a})(CH_2)_v$—,
$R^{5b}R^{12c}NN(R^{12b})COO(CH_2)_v$—, $R^{5b}R^{12b}NCOO(CH_2)_v$— or $R^{13}OCON(R^{12a})(CH_2)_v$—, where v is 0 to 2;

$R^{12a}$, $R^{12b}$ and $R^{12c}$ are independently $R^5a$. $R^{12a}$ and $R^{12b}$, or $R^{12b}$ and $R^{12c}$, or $R^{12a}$ and $R^{12c}$, or $R^{12b}$ and $R^{5b}$, or $R^{12c}$ and $R^{5b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2 and $R^1$ and $R^{10}$ are as defined;

$R^{13}$ is $C_1$–$C_6$ alkyl; substituted $C_1$–$C_6$ alkyl, where the substitutents are phenyl or substituted phenyl where the substituents on the phenyl are 1 to 3 of halogen, $C_1$–$C_6$ alkyl, $C_1$–$C_6$ alkoxy or hydroxy; phenyl; or substituted phenyl where the substituents on the phenyl are 1 to 3 of halogen, $C_1$–$C_6$ alkyl, $C_1$–$C_6$ alkoxy or hydroxy;

$R^{10}$ and $R^{11}$ are independently hydrogen, $C_1$–$C_6$ alkyl or $C_1$–$C_5$ alkanoyl-$C_1$–$C_6$ alkyl;

$R^4$, $R^{4a}$, $R^5$, $R^{5a}$ and $R^{5b}$ are independently hydrogen, $C_1$–$C_{10}$ alkyl or substituted $C_1$–$C_{10}$ alkyl where the substituents are from 1 to 3 of hydroxy, $C_1$–$C_3$ alkoxy, fluoro, phenyl independently disubstituted with $R^1$ and $R^2$, $C_1$–$C_{20}$-alkanoyloxy, $C_1$–$C_5$ alkoxycarbonyl or carboxy; where $R^1$ and $R^2$ are as defined above;

$R^6$ is hydrogen;

A is

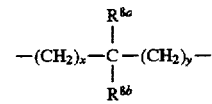

where x and y are independently 0 or 1;

$R^{8a}$ and $R^{8b}$ are independently hydrogen, $C_1$–$C_{10}$ alkyl, substituted $C_1$–$C_{10}$ alkyl where the substitutents are from 1 to 3 of imidazolyl, indolyl, hydroxy, fluoro, —$S(O)_mR^{7a}$, $C_1$–$C_6$ alkoxy, $C_3$–$C_7$ cycloalkyl, phenyl independently disubstituted with $R^1$ and $R^2$, $C_1$–$C_5$ alkanoyloxy, $C_1$–$C_5$ alkoxycarbonyl or carboxy, where $R^1$, $R^2$, $R^{7a}$, and m are as defined; or $R^{8a}$ and $R^{8b}$ can be taken together to form —$(CH_2)_t$— where t is 2; and $R^{8a}$ and $R^{8b}$ can independently be joined to $R^5$ to form alkylene bridges between the terminal nitrogen and the alkyl portion of the A group wherein the bridge contains from one to five carbon atoms;

and pharmaceutically acceptable salts thereof.

5. The stereospecific compound of claim 1 of the structural formula:

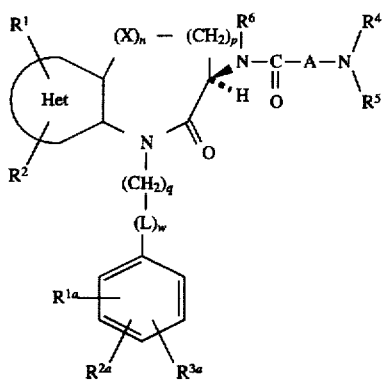

where $R^1$, $R^2$, X, n, p, q, L, w, $R^{1a}$, $R^{2a}$, $R^{3a}$, $R^4$, $R^5$, $R^6$ and A are as defined in claim .

6. A compound which is selected from the group consisting of:

3-Amino-N-[5,6,7,8-tetrahydro-5-oxo-4-[[2'-(1H-tetrazol-5-yl)[1,1'-biphenyl]-4-yl]methyl]-4H-thieno[3,2-b]azepin-6(R)-yl]-3-methylbutanamide;

N-Ethyl-4'-[[6(R)-[[3-amino-3-methyl-1-oxobutyl]amino]-5,6,7,8-tetrahydro-5-oxo-4H-thieno[3,2-b]azepin-4-yl]methyl][1,1'-biphenyl]-2-carboxamide;

3-Amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-3-methylbutanamide;

3-[2(R)-Hydroxypropyl]amino-N-[5,6,7,8-tetrahydro-5-oxo-4-[[2'-(1H-tetrazol-5-yl) [1,1'-biphenyl]-4-yl] methyl]-4H-thieno[3,2-b]azepin-6(R)-yl]-3-methylbutanamide;

N-Ethyl-4'-[[6(R)-[[3-[2(R)-hydroxypropyl]amino-3-methyl-1-oxo-butyl]amino]-5,6,7,8-tetrahydro-5-oxo-4H-thieno[3,2-b]azepin-4-yl]-methyl][1,1'-biphenyl]-2-carboxamide;

3-[2(R)-Hydroxypropyl]amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-3-methylbutanamide;

3-[2(S),3-Dihydroxypropyl]amino-N-[5,6,7,8-tetrahydro-5-oxo-4-[[2'-(1H-tetrazol-5-yl)[1,1'-biphenyl]-4-yl]methyl]-4H-thieno[3,2-b]azepin-6(R)-yl]-3-methylbutanamide;

N-Ethyl-4'-[[6(R)-[[3-[2(S),3-dihydroxypropyl]amino-3-methyl-1-oxo-butyl]amino]-5,6,7,8-tetrahydro-5-oxo-4H-thieno[3,2-b]azepin-4-yl]-methyl][1,1'-biphenyl]-2-carboxamide;

3-[2(S),3-Dihydroxypropyl]amino-N-[5,6,7,8-tetrahydro-5-oxo-4-[[2'-[[(methylamino)carbonyl]amino][1,1'-biphenyl]-4-yl]methyl]-4H-thieno[3,2-b]azepin-6(R)-yl]-3-methylbutanamide;

2-Amino-N-[5,6,7,8-tetrahydro-5-oxo-4-[[2'-(1H-tetrazol-5-yl)[1,1'-biphenyl]-4-yl]methyl]-4H-thieno[3,2-b]azepin-6(R)-yl]-2-methylpropanamide;

N-Ethyl-4'-[[6(R)-[[2-amino-2-methyl-1-oxopropyl]amino]-5,6,7,8-tetrahydro-5-oxo-4H-thieno[3,2-b]azepin-4-yl]methyl][1,1'-biphenyl]-2-carboxamide; and 2-Amino-N-[5,6,7,8-tetrahydro-5-oxo-4-[[2'-[[(methylamino)carbonyl]amino][1,1'-biphenyl]-4-yl]methyl]-4H-thieno[3,2-]azepin-6(R)-yl]-2-methylpropanamide.

* * * * *